United States Patent [19]

Mayer et al.

[11] Patent Number: 5,032,167
[45] Date of Patent: Jul. 16, 1991

[54] SUBSTITUTED SULFONYLUREAS

[75] Inventors: Horst Mayer, Ludwigshafen; Gerhard Hamprecht, Weinheim; Bruno Wuerzer, Otterstadt; Karl-Otto Westphalen, Speyer, all of Fed. Rep. of Germany

[73] Assignee: Basf, Ludwigshafen, Fed. Rep. of Germany

[21] Appl. No.: 448,984

[22] Filed: Dec. 12, 1989

[30] Foreign Application Priority Data

Dec. 15, 1988 [DE] Fed. Rep. of Germany ....... 3842177

[51] Int. Cl.$^5$ ................. C07D 239/69; C07D 401/12; C07D 413/12; A01N 43/54
[52] U.S. Cl. ........................................... 71/92; 71/90; 544/123; 544/58.6; 544/321
[58] Field of Search ...................... 71/90, 92; 544/321, 544/123

[56] References Cited

U.S. PATENT DOCUMENTS 4,671,819 6/1987 Meyer et al. ............................ 71/93

FOREIGN PATENT DOCUMENTS 0007687 2/1980 European Pat. Off. .

OTHER PUBLICATIONS

Derwent Reg. 83-755500/46 Japan Patent Disclosure 82/008500 (Published 7-28-83).

Primary Examiner—John M. Ford
Attorney, Agent, or Firm—Keil & Weinkauf

[57] ABSTRACT

Substituted sulfonylureas of the formula I

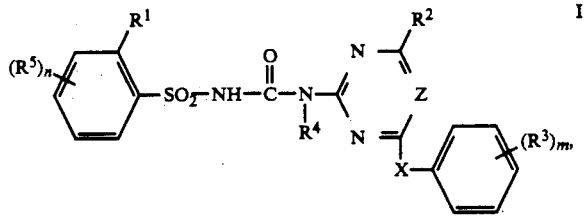

where the substituents and indices have the following meanings:

x is oxygen or sulfur;
z is nitrogen or methine (=CH—);
$R^1$ is halogen or substituted or unsubstituted $C_1$–$C_4$-alkoxycarbonyl or $C_1$–$C_3$-alkoxy, or a radical —$CONR^6R^7$, where
$R^6$ is hydrogen, $C_1$–$C_8$-alkyl or $C_1$–$C_6$-alkoxy and $R^7$ is hydrogen or $C_1$–$C_8$-alkyl;
$R^2$ is halogen or substituted or unsubstituted $C_1$–$C_4$-alkoxy or $C_1$–$C_4$-alkyl;
$R^3$ is $C_1$–$C_4$-alkyl, $C_1$–$C_4$-alkylthio, $C_1$–$C_4$-haloalkyl, $C_1$–$C_4$-haloalkoxy, $C_1$–$C_4$-haloalkylthio, halogen, cyano, nitro, amino, mono-$C_1$–$C_4$-alkylamino, di-$C_1$–$C_4$-alkylamino, $C_2$–$C_6$-alkenyl, $C_1$–$C_4$-alkoxycarbonyl, $C_1$–$C_4$-alkanoyl or benzyl; a 5- or 6-membered saturated heterocycle which is attached by its nitrogen atom and which, besides methylene and a nitrogen, may also contain an oxygen or a sulfur atom; or, bonded to adjacent ring positions, —OCRR'O—, where R and R' are each hydrogen or $C_1$–$C_4$-alkyl;
$R^4$ is hydrogen or $C_1$–$C_4$-alkyl;
$R^5$ is halogen $C_1$–$C_4$-alkyl, $C_1$–$C_4$-alkoxy, $C_1$–$C_4$-alkylthio or $C_1$–$C_4$-haloalkyl;
m is from 0 to 3 or, when $R^3$ is halogen, from 0 to 5, differences among the $R^3$ radicals being possible when m is 2 or 3; and
n is from 0 to 2, a difference between the $R^5$ radicals being possible when n is 2;

and environmentally acceptable salts thereof, processes for their manufacture, and their use as herbicidal agents.

5 Claims, No Drawings

SUBSTITUTED SULFONYLUREAS

The present invention relates to substituted sulfonylureas of the general formula I

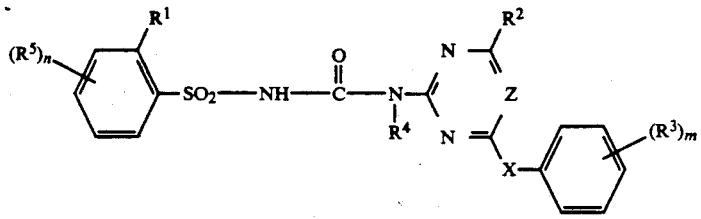

where the substituents and indices have the following meanings:

X is oxygen or sulfur;
Z is nitrogen or methine (=CH—);
$R^1$ is halogen, $C_1$-$C_4$-alkoxycarbonyl which may carry from one to three of the following radicals: halogen, $C_1$-$C_4$-alkoxy, $C_1$-$C_4$-haloalkoxy, $C_1$-$C_4$-alkylthio and/or $C_1$-$C_4$-haloalkylthio; $C_1$-$C_3$-alkoxy which may carry from one to three of the following radicals: halogen, $C_1$-$C_4$-alkoxy, $C_1$-$C_4$-haloalkoxy, $C_1$-$C_4$-alkylthio and/or $C_1$-$C_4$-haloalkylthio; or a radical —$CONR^6R^7$, where $R^6$ is hydrogen, $C_1$-$C_8$-alkyl or $C_1$-$C_6$-alkoxy and $R^7$ is hydrogen or $C_1$-$C_8$-alkyl;
$R^2$ is halogen; $C_1$-$C_4$-alkoxy or $C_1$-$C_4$-alkyl which may each carry from one to three of the following radicals: halogen, $C_1$-$C_4$-alkoxy and/or $C_1$-$C_4$-alkylthio;
$R^3$ is $C_1$-$C_4$-alkyl, $C_1$-$C_4$-alkoxy, $C_1$-$C_4$-alkylthio, $C_1$-$C_4$-haloalkoxy, $C_1$-$C_4$-haloalkylthio, halogen, cyano, nitro, amino, mono-$C_1$-$C_4$-alkylamino, di-$C_1$-$C_4$-alkylamino, $C_2$-$C_6$-alkenyl, $C_1$-$C_4$-alkoxycarbonyl, $C_1$-$C_4$-alkanoyl or benzyl; a 5- or 6-membered saturated heterocycle which is attached by its nitrogen atom and which, besides methylene and a nitrogen, may also contain an oxygen or sulfur atom; or, bonded to adjacent ring positions, —OCRR'O—, where R and R' are each hydrogen or $C_1$-$C_4$-alkyl;
$R^4$ is hydrogen or $C_1$-$C_4$-alkyl;
$R^5$ is halogen, $C_1$-$C_4$-alkyl, $C_1$-$C_4$-alkoxy, $C_1$-$C_4$-alkylthio or $C_1$-$C_4$-haloalkyl;
m is from 0 to 3 or, when $R^3$ is halogen, from 0 to 5, differences among the $R^3$ radicals being possible when m is 2 or 3; and
n is from 0 to 2, a difference between the $R^5$ radicals being possible when n is 2;

and to environmentally acceptable salts thereof.

The present invention further relates to processes for preparing compounds I and to the use thereof as herbicides.

JP-A-58/126,872 discloses pyrimidyl- and triazinyl-sulfonylureas of the formula I'

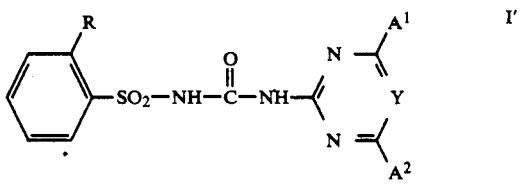

where the radicals have inter alia the following meanings;

R is substituted or unsubstituted phenyl or phenoxy,
Y is nitrogen or methine,
$A^1$ and $A^2$ are each independently of the other hydrogen, halogen, alkyl, alkoxy, haloalkyl, alkylthioalkyl, phenylthio and/or phenoxy.

However, these compounds leave a lot to be desired as herbicides on account of the low selectivity with respect to harmful plants and on account of the relatively high application rates required.

It is an object of the present invention to provide novel compounds of the class of the substituted sulfonylureas with improved herbicidal properties.

We have found that this object is achieved by the substituted sulfonylureas I defined at the beginning.

In the reaction scheme below, which indicates methods for preparing I, the radicals

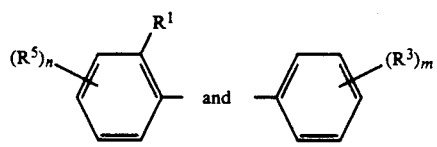

have been replaced for greater clarity by $\phi1$ and $\Phi2$ respectively.

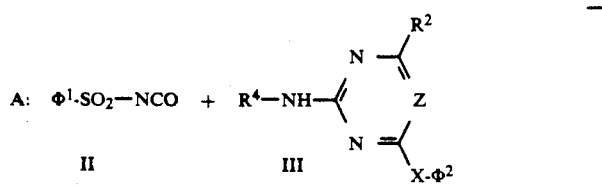

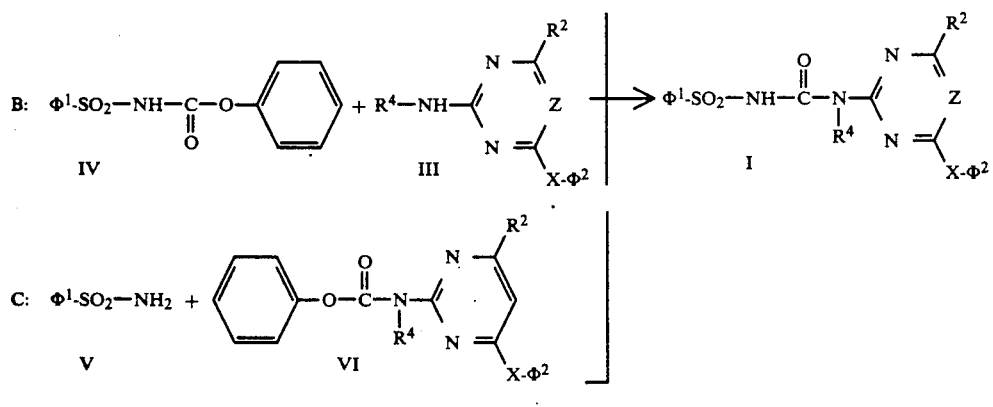

The specific conditions for each of these methods are as follows:

A: A sulfonyl isocyanate II is reacted in a conventional manner (EP-A-7687) in an inert organic solvent in the absence or presence of a base with an approximately stiochiometric amount of a 2-aminohetaryl ether III at from 0 to 120° C., preferably at from 10 to 100° C.

This reaction is preferably carried out in acetonitrile, toluene or methylene chloride in the presence of from 0 to 100 mole equivalents, preferably from 10 to 50 mole equivalents, of a tertiary amine such as 1,4-diazabicyclo[2.2.2]octane (DABCO).

B: A corresponding sulfonyl carbamate of the formula IV is reacted in a conventional manner (EP-A-120,814) in an inert organic solvent at from 0 to 120° C., preferably at from 10 to 100° C., with a 2-aminohetaryl ether III. A base, such as a tertiary amine base, may be added here to speed up the reaction and improve the quality of the product.

This variation is preferably carried out in an aprotic polar solvent such as dioxane or tetrahydrofuran in the presence of a teritary amine such as p-dimethylaminopyridine and 1,4-diazabicyclo[2.2.2]octane.

C: A sulfonamide of the formula V is reacted in a conventional manner (EP-A-120,814) in an inert organic solvent with an approximately stoichiometric amount of phenyl carbamate VI at from 0 to 120° C., preferably at from 25 to 100° C. Again it is possible to add a base such as a tertiary amine. Particularly suitable tertiary amines for this purpose are pyridine, the picolines, 2,4-and 2,6-lutidine, 2,4,6-collidine, p-dimethylaminopyridine, 1,4-diazabicyclo[2.2.2]octane (DABCO) and 1,8-diazabicyclo[5.5.0]undec-7-ene, preferably 1,4-diazabicyclo[2.2.2]octane and 1,8-diazabicyclo[5.4.0]undec-7-ene.

Again it is advantageous to use a solvent such as dioxane or tetrahydrofuran.

Preferably, the reaction is carried out under atmospheric pressure or under a slightly superatmospheric pressure, for example at up to 5 bar, either batchwise or continuously.

The salts of the sulfonylureas are obtained by reaction with a stoichiometric amount of a metal alcoholate in the absence or presence of an inert organic solvent.

The sulfonamides of the formula V required as starting materials can be prepared from haloanthranilic esters by a Meerwein reaction (F. Muth in Methoden der Organischem Chemie (Houben-Weyl) volume 9, 557 (1955)) and subsequent reaction of the resulting sulfonyl chloride with ammonia.

The aryloxy- or thioaryl-substituted pyrimidine or triazine intermediates required can be prepared by literature methods, as described for example in J. Med. Chem. 29 (1986), 676, in J. Amer. Chem. Soc. 73 (1951), 2990, in Arch. Pharm. 296 (1963), 151, in Chem. Ber. 96 (1963), 2909, in Bull. Chem. Soc. Jpn. 45 (1972), 3133, in Agric. Biol. Chem. 30 (1966) 896, and in Rec. Trav. Chim. Pays-Bas 64 (1945), 115, or similarly to the Examples given in the test below.

As regards biological activity, preference is given to the compounds of the formula I where substituents have the following meanings:

X is oxygen or sulfur;

Z is nitrogen or methine (=CH—);

$R^1$ is halogen such as fluorine, chlorine or bromine, in particular chlorine, alkoxycarbonyl such as methoxycarbonyl, ethoxycarbonyl, propyloxycarbonyl, isopropyloxycarbonyl or butoxycarbonyl, in particular methoxycarbonyl or ethoxycarbonyl, alkoxy such as methoxy, ethoxy, propyloxy or 1-methylethoxy, in particular ethoxy or 1-methylethoxy, which may each carry halogen as mentioned above, alkoxy as mentioned above and also haloalkoxy such as trifluoromethoxy, difluromethoxy, fluoromethoxy, trichloromethoxy, dichloromethoxy, chloromethoxy, difluorochloromethoxy, 1-fluoroethoxy, 2-fluoroethoxy or 2,2,2-trifluoroethoxy, but in particular trifluoromethoxy or difluoromethoxy, alkylthio such as methylthio, ethylthio, propylthio or 1-methylethylthio, in particular methylthio, ethylthio and/or haloalkylthio such as trifluoromethylthio, fluoromethylthio, 1-trifluoromethylthio, fluoromethylthio, 1-fluoroethylthio, 2-fluoroethylthio, chloromethylthio or 2-chloromethylthio, but in particular trifluoromethylthio, chloromethylthio or 2-chloromethylthio, preferably in the 1- or 2-position, or corresponding alkoxy, and further butyloxy, 1-methylpropyloxy, 2-methylpropyloxy or 1,1-dimethylethoxy, preferably in the 2- or 3-position; carbamoyl such as carboxyamide, N-methylcarbamoyl, N,N-dimethylcarbamoyl, N-ethylcarbamoyl, N,N-diethylcarbamoyl, N-ethyl-N-methylcarbamoy, in particular N-methyl- and N,N-dimethyl-carbamoyl; or hydroxamic ester groups, such as N-methoxycarbamoyl, N-methoxy-N-methylcarbamoyl or N-ethoxycarbamoyl, preferably N-methoxy-N-methylcarbamoyl;

$R^2$ is halogen as mentioned under $R^1$, preferably chlorine; alkoxy as mentioned under $R^1$, preferably methoxy; alkyl such as methyl, ethyl, propyl, 1-methylethyl, butyl, 1-methylpropyl, 2-methylpropyl or 1,1-dimethylpropyl, but in particular methyl or ethyl, which may each be monosubstituted, disubstituted or trisubstituted by halogen and/or alkoxy such as mentioned under $R^1$ and/or by alkylthio such as methylthio, ethylthion, propylthio or 1-methylethylthio;

$R^3$ is alkyl as mentioned under $R^2$, preferably methyl or ethyl; alkoxy as mentioned under $R^1$, preferably methoxy, ethoxy or 1-methylethoxy; alkylthio as mentioned under $R^2$, in particular methylthio or ethylthio; haloalkyl such as trifluoromethyl, difluoromethyl, fluoromethyl, trichloromethyl, dichloromethyl, chloromethyl, difluorochloromethyl, 1-fluoroethyl, 2-fluoroethyl or 2,2,2-trifluoroethyl, in particular trifluoromethyl or difluoromethyl; haloalkoxy as mentioned under $R^1$, preferably 2-chloroethoxy or 2-fluoroethoxy; haloalkylthio as mentioned under $R^1$, preferably 2-chloroethylthio or 2-fluoroethylthio; halogen as mentioned under $R^1$, in particular fluorine or chlorine, cyano, nitro, amino and/or amino which is monosubstituted or disubstituted by the abovementioned alkyl, such as methylamino, dimethylamino, ethylamino, diethylamino, methylethylamino, propylamino, N-methyl-N-propylamino, N-ethyl-N-propylamino, N,N-dipropylamino or N,N-di(1-methylethyl)amino, in particular N,N-dimethylamino; alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular ethenyl, 1-propenyl, 2-propenyl or 1-methylethenyl; alkoxycarbonyl as mentioned in general and in particular under $R^1$; $C_1-C_4$-alkanoyl such as propionyl and particularly acetyl and pivaloyl, or benzyl; a 5- or 6-membered saturated heterocycle which is attached by its nitrogen atom and which, besides methylene and nitrogen, may also contain an oxygen or sulfur atom, such aspyrrolidinyl, piperidinyl, morpholinyl or thiomorpholinyl; or, bonded to adjacent ring positions, —O—CRR'—O—, where R and R' are each hydrogen or alkyl as mentioned under $R^3$, preferably hydrogen, methyl or ethyl;

the number of $R^3$ substituents is from 0 to 3, but preferably 0, 1 or 2 or from 0 to 5 when $R^3$ is halogen, and the groups may differ from each other when m is equal to or greater than 2;

$R^4$ is hydrogen or alkyl as mentioned under $R^2$, preferably hydrogen or methyl; and $R^5$ is halogen, alkyl, alkoxy, alkylthio or haloalkyl as mentioned under $R^3$.

The number of $R^5$ substituents is from 0 to 2, and the groups may differ from each other when n is 2.

Particularly active compounds of the formula I are given in Tables A, B, C and D below.

TABLE A

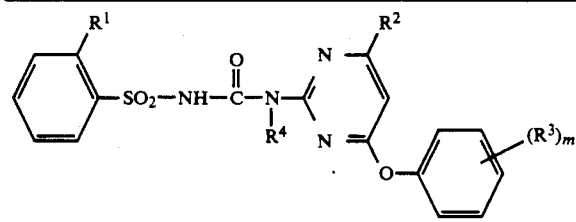

| $R^1$ | $R^4$ | $R^2$ | $(R^3)_m$ |
|---|---|---|---|
| CO$_2$CH$_3$ | H | Cl | H |
| CO$_2$CH$_3$ | H | Cl | 3-CH$_3$ |
| CO$_2$CH$_3$ | H | Cl | 3-OCH$_3$ |
| CO$_2$CH$_3$ | H | Cl | 3-CF$_3$ |
| CO$_2$CH$_3$ | H | Cl | 2-F |
| CO$_2$CH$_3$ | H | Cl | 2-Cl |
| CO$_2$CH$_3$ | H | Cl | 3-Cl |
| CO$_2$CH$_3$ | H | Cl | 3-NO$_2$ |
| CO$_2$CH$_3$ | H | Cl | 4-NO$_2$ |
| CO$_2$CH$_3$ | H | Cl | 2-CN |
| CO$_2$CH$_3$ | H | Cl | 2,6-OCH$_3$,OCH$_3$ |
| CO$_2$CH$_3$ | H | Cl | 2,4,6-Cl,Cl,Cl |
| CO$_2$CH$_3$ | H | Cl | 2-Cl,4-CF$_3$ |
| CO$_2$CH$_3$ | H | Cl | 3-N(CH$_3$)$_2$ |
| CO$_2$CH$_3$ | CH$_3$ | Cl | H |
| CO$_2$CH$_3$ | CH$_3$ | Cl | 3-CH$_3$ |
| CO$_2$CH$_3$ | CH$_3$ | Cl | 3-OCH$_3$ |
| CO$_2$CH$_3$ | CH$_3$ | Cl | 3-CF$_3$ |
| CO$_2$CH$_3$ | CH$_3$ | Cl | 2-F |
| CO$_2$CH$_3$ | CH$_3$ | Cl | 2-Cl |
| CO$_2$CH$_3$ | CH$_3$ | Cl | 3-Cl |
| CO$_2$CH$_3$ | CH$_3$ | Cl | 3-NO$_2$ |
| CO$_2$CH$_3$ | CH$_3$ | Cl | 4-NO$_2$ |
| CO$_2$CH$_3$ | CH$_3$ | Cl | 2-CN |
| CO$_2$CH$_3$ | CH$_3$ | Cl | 2,6-OCH$_3$,OCH$_3$ |
| CO$_2$CH$_3$ | CH$_3$ | Cl | 2,4,6-Cl,Cl,Cl |
| CO$_2$CH$_3$ | CH$_3$ | Cl | 2-Cl,4-CF$_3$ |
| CO$_2$CH$_3$ | CH$_3$ | Cl | 3-N(CH$_3$)$_2$ |
| CO$_2$CH$_3$ | H | CH$_3$ | H |
| CO$_2$CH$_3$ | H | CH$_3$ | 3-CH$_3$ |
| CO$_2$CH$_3$ | H | CH$_3$ | 3-OCH$_3$ |
| CO$_2$CH$_3$ | H | CH$_3$ | 3-CF$_3$ |
| CO$_2$CH$_3$ | H | CH$_3$ | 2-F |
| CO$_2$CH$_3$ | H | CH$_3$ | 2-Cl |
| CO$_2$CH$_3$ | H | CH$_3$ | 3-Cl |
| CO$_2$CH$_3$ | H | CH$_3$ | 3-NO$_2$ |
| CO$_2$CH$_3$ | H | CH$_3$ | 4-NO$_2$ |
| CO$_2$CH$_3$ | H | CH$_3$ | 2-CN |
| CO$_2$CH$_3$ | H | CH$_3$ | 2,6-OCH$_3$,OCH$_3$ |
| CO$_2$CH$_3$ | H | CH$_3$ | 2,4,6-Cl,Cl,Cl |
| CO$_2$CH$_3$ | H | CH$_3$ | 2-Cl,4-CF$_3$ |
| CO$_2$CH$_3$ | H | CH$_3$ | 3-N(CH$_3$)$_2$ |
| CO$_2$CH$_3$ | H | CF$_3$ | H |
| CO$_2$CH$_3$ | H | CF$_3$ | 3-CH$_3$ |
| CO$_2$CH$_3$ | H | CF$_3$ | 3-OCH$_3$ |
| CO$_2$CH$_3$ | H | CF$_3$ | 3-CF$_3$ |
| CO$_2$CH$_3$ | H | CF$_3$ | 2-F |
| CO$_2$CH$_3$ | H | CF$_3$ | 2-Cl |

TABLE A-continued

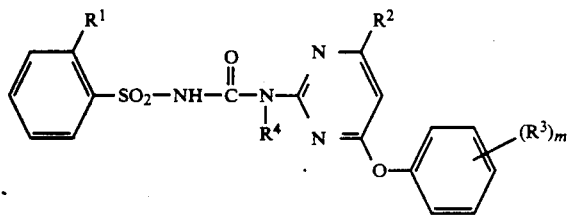

| $R^1$ | $R^4$ | $R^2$ | $(R^3)_m$ |
|---|---|---|---|
| CO₂CH₃ | H | CF₃ | 3-Cl |
| CO₂CH₃ | H | CF₃ | 3-NO₂ |
| CO₂CH₃ | H | CF₃ | 4-NO₂ |
| CO₂CH₃ | H | CF₃ | 2-CN |
| CO₂CH₃ | H | CF₃ | 2,6-OCH₃,OCH₃ |
| CO₂CH₃ | H | CF₃ | 2,4,6-Cl,Cl,Cl |
| CO₂CH₃ | H | CF₃ | 2-Cl,4-CF₃ |
| CO₂CH₃ | H | CF₃ | 3-N(CH₃)₂ |
| CO₂CH₃ | H | OCH₃ | 2-OCH₃ |
| CO₂CH₃ | H | OCH₃ | 4-OCH₃ |
| CO₂CH₃ | H | OCH₃ | 2-OCH₂CH₃ |
| CO₂CH₃ | H | OCH₃ | 3-OCH₂CH₃ |
| CO₂CH₃ | H | OCH₃ | 4-OCH₂CH₃ |
| CO₂CH₃ | H | OCH₃ | 2-OCH(CH₃)₂ |
| CO₂CH₃ | H | OCH₃ | 3-OCH(CH₃)₂ |
| CO₂CH₃ | H | OCH₃ | 4-OCH(CH₃)₂ |
| CO₂CH₃ | H | OCH₃ | 2-O(CH₂)₂CH₃ |
| CO₂CH₃ | H | OCH₃ | 3-O(CH₂)₂CH₃ |
| CO₂CH₃ | H | OCH₃ | 4-O(CH₂)₂CH₃ |
| CO₂CH₃ | H | OCH₃ | 2-OC(CH₃)₃ |
| CO₂CH₃ | H | OCH₃ | 3-OC(CH₃)₃ |
| CO₂CH₃ | H | OCH₃ | 4-OC(CH₃)₃ |
| CO₂CH₃ | H | OCH₃ | 2,3-OCH₃,OCH₃ |
| CO₂CH₃ | H | OCH₃ | 2,4-OCH₃,OCH₃ |
| CO₂CH₃ | H | OCH₃ | 2,5-OCH₃,OCH₃ |
| CO₂CH₃ | H | OCH₃ | 3,4-OCH₃,OCH₃ |
| CO₂CH₃ | H | OCH₃ | 3,5-OCH₃,OCH₃ |
| CO₂CH₃ | H | OCH₃ | 2,3,4-OCH₃,OCH₃,OCH₃ |
| CO₂CH₃ | H | OCH₃ | 2,3,5-OCH₃,OCH₃,OCH₃ |
| CO₂CH₃ | H | OCH₃ | 2,4,6-OCH₃,OCH₃,OCH₃ |
| CO₂CH₃ | H | OCH₃ | 3,4,5-OCH₃,OCH₃,OCH₃ |
| CO₂CH₃ | H | OCH₃ | H |
| CO₂CH₃ | H | OCH₃ | 3-CH₃ |
| CO₂CH₃ | H | OCH₃ | 3-OCH₃ |
| CO₂CH₃ | H | OCH₃ | 3-CF₃ |
| CO₂CH₃ | H | OCH₃ | 2-F |
| CO₂CH₃ | H | OCH₃ | 2-Cl |
| CO₂CH₃ | H | OCH₃ | 3-Cl |
| CO₂CH₃ | H | OCH₃ | 3-NO₂ |
| CO₂CH₃ | H | OCH₃ | 4-NO₂ |
| CO₂CH₃ | H | OCH₃ | 2-CN |
| CO₂CH₃ | H | OCH₃ | 2,6-OCH₃,OCH₃ |
| CO₂CH₃ | H | OCH₃ | 2,4,6-Cl,Cl,Cl |
| CO₂CH₃ | H | OCH₃ | 2-Cl,4-CF₃ |
| CO₂CH₃ | H | OCH₃ | 3-N(CH₃)₂ |
| Cl | H | Cl | H |
| Cl | H | Cl | 3-CH₃ |
| Cl | H | Cl | 3-OCH₃ |
| Cl | H | Cl | 3-CF₃ |
| Cl | H | Cl | 2-F |
| Cl | H | Cl | 2-Cl |
| Cl | H | Cl | 3-Cl |
| Cl | H | Cl | 3-NO₂ |
| Cl | H | Cl | 4-NO₂ |
| Cl | H | Cl | 2-CN |
| Cl | H | Cl | 2,6-OCH₃,OCH₃ |
| Cl | H | Cl | 2,4,6-Cl,Cl,Cl |
| Cl | H | Cl | 2-Cl,4-CF₃ |
| Cl | H | Cl | 3-N(CH₃)₂ |
| Cl | CH₃ | Cl | H |
| Cl | CH₃ | Cl | 3-CH₃ |
| Cl | CH₃ | Cl | 3-OCH₃ |
| Cl | CH₃ | Cl | 3-CF₃ |
| Cl | CH₃ | Cl | 2-F |
| Cl | CH₃ | Cl | 2-Cl |
| Cl | CH₃ | Cl | 3-Cl |
| Cl | CH₃ | Cl | 3-NO₂ |
| Cl | CH₃ | Cl | 4-NO₂ |
| Cl | CH₃ | Cl | 2-CN |
| Cl | CH₃ | Cl | 2,6-OCH₃,OCH₃ |
| Cl | CH₃ | Cl | 2,4,6-Cl,Cl,Cl |
| Cl | CH₃ | Cl | 2-Cl,4-CF₃ |
| Cl | CH₃ | Cl | 3-N(CH₃)₂ |
| Cl | H | CH₃ | H |
| Cl | H | CH₃ | 3-CH₃ |
| Cl | H | CH₃ | 3-OCH₃ |
| Cl | H | CH₃ | 3-CF₃ |
| Cl | H | CH₃ | 2-F |
| Cl | H | CH₃ | 2-Cl |
| Cl | H | CH₃ | 3-Cl |
| Cl | H | CH₃ | 3-NO₂ |
| Cl | H | CH₃ | 4-NO₂ |
| Cl | H | CH₃ | 2-CN |
| Cl | H | CH₃ | 2,6-OCH₃,OCH₃ |
| Cl | H | CH₃ | 2,4,6-Cl,Cl,Cl |
| Cl | H | CH₃ | 2-Cl,4-CF₃ |
| Cl | H | CH₃ | 3-N(CH₃)₂ |
| Cl | H | CF₃ | H |
| Cl | H | CF₃ | 3-CH₃ |
| Cl | H | CF₃ | 3-OCH₃ |
| Cl | H | CF₃ | 3-CF₃ |
| Cl | H | CF₃ | 2-F |
| Cl | H | CF₃ | 2-Cl |
| Cl | H | CF₃ | 3-Cl |
| Cl | H | CF₃ | 3-NO₂ |
| Cl | H | CF₃ | 4-NO₂ |
| Cl | H | CF₃ | 2-CN |
| Cl | H | CF₃ | 2,6-OCH₃,OCH₃ |
| Cl | H | CF₃ | 2,4,6-Cl,Cl,Cl |
| Cl | H | CF₃ | 2-Cl,4-CF₃ |
| Cl | H | CF₃ | 3-N(CH₃)₂ |
| Cl | H | OCH₃ | H |
| Cl | H | OCH₃ | 3-CH₃ |
| Cl | H | OCH₃ | 3-OCH₃ |
| Cl | H | OCH₃ | 3-CF₃ |
| Cl | H | OCH₃ | 2-F |
| Cl | H | OCH₃ | 2-Cl |
| Cl | H | OCH₃ | 3-Cl |
| Cl | H | OCH₃ | 3-NO₂ |
| Cl | H | OCH₃ | 4-NO₂ |
| Cl | H | OCH₃ | 2-CN |
| Cl | H | OCH₃ | 2,6-OCH₃,OCH₃ |
| Cl | H | OCH₃ | 2,4,6-Cl,Cl,Cl |
| Cl | H | OCH₃ | 2-Cl,4-CF₃ |
| Cl | H | OCH₃ | 3-N(CH₃)₂ |
| Cl | H | OCH₃ | 2-OCH₃ |
| Cl | H | OCH₃ | 4-OCH₃ |
| Cl | H | OCH₃ | 2-OCH₂CH₃ |
| Cl | H | OCH₃ | 3-OCH₂CH₃ |
| Cl | H | OCH₃ | 4-OCH₂CH₃ |
| Cl | H | OCH₃ | 2-OCH(CH₃)₂ |
| Cl | H | OCH₃ | 3-OCH(CH₃)₂ |
| Cl | H | OCH₃ | 4-OCH(CH₃)₂ |
| Cl | H | OCH₃ | 2-O(CH₂)₂CH₃ |
| Cl | H | OCH₃ | 3-O(CH₂)₂CH₃ |
| Cl | H | OCH₃ | 4-O(CH₂)₂CH₃ |
| Cl | H | OCH₃ | 2-OC(CH₃)₃ |
| Cl | H | OCH₃ | 3-OC(CH₃)₃ |
| Cl | H | OCH₃ | 4-OC(CH₃)₃ |
| Cl | H | OCH₃ | 2,3-OCH₃,OCH₃ |
| Cl | H | OCH₃ | 2,4-OCH₃,OCH₃ |
| Cl | H | OCH₃ | 2,5-OCH₃,OCH₃ |
| Cl | H | OCH₃ | 3,4-OCH₃,OCH₃ |
| Cl | H | OCH₃ | 3,5-OCH₃,OCH₃ |
| Cl | H | OCH₃ | 2,3,4-OCH₃,OCH₃,OCH₃ |
| Cl | H | OCH₃ | 2,3,5-OCH₃,OCH₃,OCH₃ |
| Cl | H | OCH₃ | 2,4,6-OCH₃,OCH₃,OCH₃ |
| Cl | H | OCH₃ | 3,4,5-OCH₃,OCH₃,OCH₃ |
| CO₂C₂H₅ | H | Cl | H |
| CO₂C₂H₅ | H | CH₃ | 3-SCH₃ |

TABLE A-continued

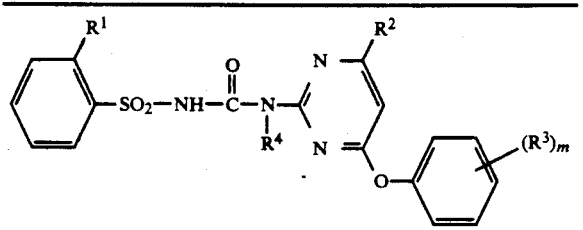

| R¹ | R⁴ | R² | (R³)ₘ |
|---|---|---|---|
| CO₂C₂H₅ | CH₃ | CH₃ | 2-O(CH₂)₂Cl |
| CO₂C₂H₅ | H | Cl | 3-OCCl₃ |
| CO₂C₂H₅ | H | OCH₃ | 4-OCH₂F |
| CO₂C₂H₅ | H | OCH₃ | 4-OCHF₂ |
| CO₂C₃H₇ | H | CF₃ | 3-O(CH₂)₂F |
| CO₂C₃H₇ | H | CF₃ | 2-S(CH₂)₂Cl |
| CO₂C₃H₇ | H | CCl₃ | 2-S(CH₂)₂F |
| CO₂C₃H₇ | H | CH₃ | 2-SCF₃ |
| CO₂C₃H₇ | CH₃ | Cl | 4-SCHF₂ |
| CONH(CH₃) | H | Cl | 2-OCH₃ |
| CONH(CH₃) | H | CH₃ | 3-OCH₃ |
| CON(CH₃)₂ | H | Cl | 2-OCH₃ |
| CON(CH₃)₂ | H | CH₃ | 3-OCH₃ |
| CON(CH₃)₂ | H | OCH₃ | 4-OCH₃ |
| CON(CH₃)₂ | H | CF₃ | 2-OCH₃ |
| CON(CH₃)₂ | H | OC₂H₅ | 2-SCH₃ |
| CON(CH₃)₂ | H | OC₂H₅ | 3-OCF₃ |
| CON(CH₃)OCH₃ | H | CH₃ | 2-OCH₃ |
| CON(CH₃)OCH₃ | H | OCH₃ | 3-OCH₃ |
| CON(CH₃)OCH₃ | H | Cl | 2-OCH₃ |
| CO₂(CH₂)₂Cl | H | Cl | 2-N(CH₃)₂ |
| CO₂(CH₂)₂OCH₃ | H | Cl | 2-CN |
| CO₂(CH₂)₂OC₂H₅ | CH₃ | Cl | 2-NO₂ |
| CO₂(CH₂)₂OCF₃ | H | Cl | 2,3-Cl,Cl |
| OCH₃ | H | Cl | 2-Cl |
| OCH₃ | H | Cl | 3-NO₂ |
| OC₂H₅ | H | Cl | 4-CN |
| O(CH₂)₂Cl | H | CH₃ | 3-CH₃ |
| O(CH₂)₂F | CH₃ | CH₃ | 2-Cl,4-CF₃ |
| O(CH₂)₂OCH₃ | CH₃ | CH₃ | 2,3,5-Cl,Cl,Cl |
| O(CH₂)₂OCH₃ | CH₃ | CH₃ | 3-N(CH₃)₂ |
| O(CH₂)₂SCH₃ | CH₃ | CH₃ | 4-OCH₃ |
| O(CH₂)₂SCH₃ | CH₃ | OCH₃ | 2,4-Cl,Cl |
| O(CH₂)₂SCF₃ | CH₃ | OCH₃ | 2-OCH₃ |

TABLE B

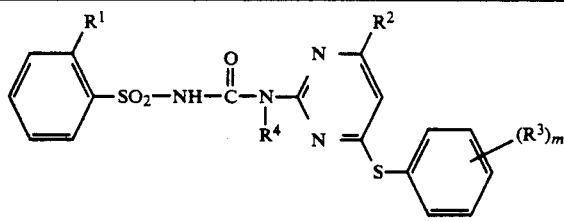

| R¹ | R⁴ | R² | (R³)ₘ |
|---|---|---|---|
| CO₂CH₃ | H | Cl | H |
| CO₂CH₃ | H | Cl | 3-CH₃ |
| CO₂CH₃ | H | Cl | 3-OCH₃ |
| CO₂CH₃ | H | Cl | 3-CF₃ |
| CO₂CH₃ | H | Cl | 2-F |
| CO₂CH₃ | H | Cl | 2-Cl |
| CO₂CH₃ | H | Cl | 3-Cl |
| CO₂CH₃ | H | Cl | 3-NO₂ |
| CO₂CH₃ | H | Cl | 4-NO₂ |
| CO₂CH₃ | H | Cl | 2-CN |
| CO₂CH₃ | H | Cl | 2,6-OCH₃,OCH₃ |
| CO₂CH₃ | H | Cl | 2,4,6-Cl,Cl,Cl |
| CO₂CH₃ | H | Cl | 2-Cl,4-CF₃ |
| CO₂CH₃ | H | Cl | 3-N(CH₃)₂ |
| CO₂CH₃ | CH₃ | Cl | H |
| CO₂CH₃ | CH₃ | Cl | 3-CH₃ |
| CO₂CH₃ | CH₃ | Cl | 3-OCH₃ |
| CO₂CH₃ | CH₃ | Cl | 3-CF₃ |
| CO₂CH₃ | CH₃ | Cl | 2-F |

TABLE B-continued

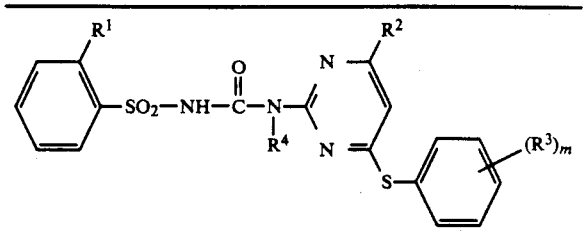

| R¹ | R⁴ | R² | (R³)ₘ |
|---|---|---|---|
| CO₂CH₃ | CH₃ | Cl | 2-Cl |
| CO₂CH₃ | CH₃ | Cl | 3-Cl |
| CO₂CH₃ | CH₃ | Cl | 3-NO₂ |
| CO₂CH₃ | CH₃ | Cl | 4-NO₂ |
| CO₂CH₃ | CH₃ | Cl | 2-CN |
| CO₂CH₃ | CH₃ | Cl | 2,6-OCH₃,OCH₃ |
| CO₂CH₃ | CH₃ | Cl | 2,4,6-Cl,Cl,Cl |
| CO₂CH₃ | CH₃ | Cl | 2-Cl,4-CF₃ |
| CO₂CH₃ | CH₃ | Cl | 3-N(CH₃)₂ |
| CO₂CH₃ | H | CH₃ | H |
| CO₂CH₃ | H | CH₃ | 3-CH₃ |
| CO₂CH₃ | H | CH₃ | 3-OCH₃ |
| CO₂CH₃ | H | CH₃ | 3-CF₃ |
| CO₂CH₃ | H | CH₃ | 2-F |
| CO₂CH₃ | H | CH₃ | 2-Cl |
| CO₂CH₃ | H | CH₃ | 3-Cl |
| CO₂CH₃ | H | CH₃ | 3-NO₂ |
| CO₂CH₃ | H | CH₃ | 4-NO₂ |
| CO₂CH₃ | H | CH₃ | 2-CN |
| CO₂CH₃ | H | CH₃ | 2,6-OCH₃,OCH₃ |
| CO₂CH₃ | H | CH₃ | 2,4,6-Cl,Cl,Cl |
| CO₂CH₃ | H | CH₃ | 2-Cl,4-CF₃ |
| CO₂CH₃ | H | CH₃ | 3-N(CH₃)₂ |
| CO₂CH₃ | H | CF₃ | H |
| CO₂CH₃ | H | CF₃ | 3-CH₃ |
| CO₂CH₃ | H | CF₃ | 3-OCH₃ |
| CO₂CH₃ | H | CF₃ | 3-CF₃ |
| CO₂CH₃ | H | CF₃ | 2-F |
| CO₂CH₃ | H | CF₃ | 2-Cl |
| CO₂CH₃ | H | CF₃ | 3-Cl |
| CO₂CH₃ | H | CF₃ | 3-NO₂ |
| CO₂CH₃ | H | CF₃ | 4-NO₂ |
| CO₂CH₃ | H | CF₃ | 2-CN |
| CO₂CH₃ | H | CF₃ | 2,6-OCH₃,OCH₃ |
| CO₂CH₃ | H | CF₃ | 2,4,6-Cl,Cl,Cl |
| CO₂CH₃ | H | CF₃ | 2-Cl,4-CF₃ |
| CO₂CH₃ | H | CF₃ | 3-N(CH₃)₂ |
| CO₂CH₃ | H | OCH₃ | H |
| CO₂CH₃ | H | OCH₃ | 3-CH₃ |
| CO₂CH₃ | H | OCH₃ | 3-OCH₃ |
| CO₂CH₃ | H | OCH₃ | 3-CF₃ |
| CO₂CH₃ | H | OCH₃ | 2-F |
| CO₂CH₃ | H | OCH₃ | 2-Cl |
| CO₂CH₃ | H | OCH₃ | 3-Cl |
| CO₂CH₃ | H | OCH₃ | 3-NO₂ |
| CO₂CH₃ | H | OCH₃ | 4-NO₂ |
| CO₂CH₃ | H | OCH₃ | 2-CN |
| CO₂CH₃ | H | OCH₃ | 2,6-OCH₃,OCH₃ |
| CO₂CH₃ | H | OCH₃ | 2,4,6-Cl,Cl,Cl |
| CO₂CH₃ | H | OCH₃ | 2-Cl,4-CF₃ |
| CO₂CH₃ | H | OCH₃ | 3-N(CH₃)₂ |
| Cl | H | Cl | H |
| Cl | H | Cl | 3-CH₃ |
| Cl | H | Cl | 3-OCH₃ |
| Cl | H | Cl | 3-CF₃ |
| Cl | H | Cl | 2-F |
| Cl | H | Cl | 2-Cl |
| Cl | H | Cl | 3-Cl |
| Cl | H | Cl | 3-NO₂ |
| Cl | H | Cl | 4-NO₂ |
| Cl | H | Cl | 2-CN |
| Cl | H | Cl | 2,6-OCH₃,OCH₃ |
| Cl | H | Cl | 2,4,6-Cl,Cl,Cl |
| Cl | H | Cl | 2-Cl,4-CF₃ |
| Cl | H | Cl | 3-N(CH₃)₂ |
| Cl | CH₃ | Cl | H |
| Cl | CH₃ | Cl | 3-CH₃ |
| Cl | CH₃ | Cl | 3-OCH₃ |
| Cl | CH₃ | Cl | 3-CF₃ |
| Cl | CH₃ | Cl | 2-F |

TABLE B-continued

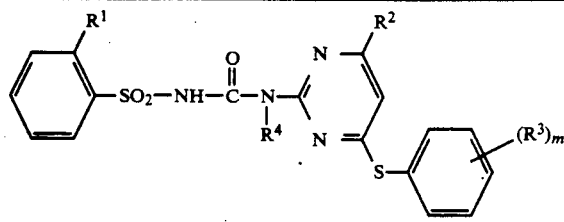

| R¹ | R⁴ | R² | (R³)ₘ |
|---|---|---|---|
| Cl | CH₃ | Cl | 2-Cl |
| Cl | CH₃ | Cl | 3-Cl |
| Cl | CH₃ | Cl | 3-NO₂ |
| Cl | CH₃ | Cl | 4-NO₂ |
| Cl | CH₃ | Cl | 2-CN |
| Cl | CH₃ | Cl | 2,6-OCH₃,OCH₃ |
| Cl | CH₃ | Cl | 2,4,6-Cl,Cl,Cl |
| Cl | CH₃ | Cl | 2-Cl,4-CF₃ |
| Cl | CH₃ | Cl | 3-N(CH₃)₂ |
| Cl | H | CH₃ | H |
| Cl | H | CH₃ | 3-CH₃ |
| Cl | H | CH₃ | 3-OCH₃ |
| Cl | H | CH₃ | 3-CF₃ |
| Cl | H | CH₃ | 2-F |
| Cl | H | CH₃ | 2-Cl |
| Cl | H | CH₃ | 3-Cl |
| Cl | H | CH₃ | 3-NO₂ |
| Cl | H | CH₃ | 4-NO₂ |
| Cl | H | CH₃ | 2-CN |
| Cl | H | CH₃ | 2,6-OCH₃,OCH₃ |
| Cl | H | CH₃ | 2,4,6-Cl,Cl,Cl |
| Cl | H | CH₃ | 2-Cl,4-CF₃ |
| Cl | H | CH₃ | 3-N(CH₃)₂ |
| Cl | H | CF₃ | H |
| Cl | H | CF₃ | 3-CH₃ |
| Cl | H | CF₃ | 3-OCH₃ |
| Cl | H | CF₃ | 3-CF₃ |
| Cl | H | CF₃ | 2-F |
| Cl | H | CF₃ | 2-Cl |
| Cl | H | CF₃ | 3-Cl |
| Cl | H | CF₃ | 3-NO₂ |
| Cl | H | CF₃ | 4-NO₂ |
| Cl | H | CF₃ | 2-CN |
| Cl | H | CF₃ | 2,6-OCH₃,OCH₃ |
| Cl | H | CF₃ | 2,4,6-Cl,Cl,Cl |
| Cl | H | CF₃ | 2-Cl,4-CF₃ |
| Cl | H | CF₃ | 3-N(CH₃)₂ |
| Cl | H | OCH₃ | H |
| Cl | H | OCH₃ | 3-CH₃ |
| Cl | H | OCH₃ | 3-OCH₃ |
| Cl | H | OCH₃ | 3-CF₃ |
| Cl | H | OCH₃ | 2-F |
| Cl | H | OCH₃ | 2-Cl |
| Cl | H | OCH₃ | 3-Cl |
| Cl | H | OCH₃ | 3-NO₂ |
| Cl | H | OCH₃ | 4-NO₂ |
| Cl | H | OCH₃ | 2-CN |
| Cl | H | OCH₃ | 2,6-OCH₃,OCH₃ |
| Cl | H | OCH₃ | 2,4,6-Cl,Cl,Cl |
| Cl | H | OCH₃ | 2-Cl,4-CF₃ |
| Cl | H | OCH₃ | 3-N(CH₃)₂ |
| CO₂C₂H₅ | H | Cl | H |
| CO₂C₂H₅ | H | CH₃ | 3-SCH₃ |
| CO₂C₂H₅ | CH₃ | CH₃ | 2-O(CH₂)₂Cl |
| CO₂C₂H₅ | H | Cl | 3-OCCl₃ |
| CO₂C₂H₅ | H | OCH₃ | 4-OCH₂F |
| CO₂C₂H₅ | H | OCH₃ | 4-OCHF₂ |
| CO₂C₃H₇ | H | CF₃ | 3-O(CH₂)₂F |
| CO₂C₃H₇ | H | CF₃ | 2-S(CH₂)₂Cl |
| CO₂C₃H₇ | H | CCl₃ | 2-S(CH₂)₂F |
| CO₂C₃H₇ | H | CH₃ | 2-SCF₃ |
| CO₂C₃H₇ | CH₃ | Cl | 4-SCHF₂ |
| CONH(CH₃) | H | Cl | 2-OCH₃ |
| CONH(CH₃) | H | CH₃ | 3-OCH₃ |
| CON(CH₃)₂ | H | Cl | 2-OCH₃ |
| CON(CH₃)₂ | H | CH₃ | 3-OCH₃ |
| CON(CH₃)₂ | H | OCH₃ | 4-OCH₃ |
| CON(CH₃)₂ | H | CF₃ | 2-OCH₃ |
| CON(CH₃)₂ | H | OC₂H₅ | 2-SCH₃ |
| CON(CH₃)₂ | H | OC₂H₅ | 3-OCF₃ |

TABLE B-continued

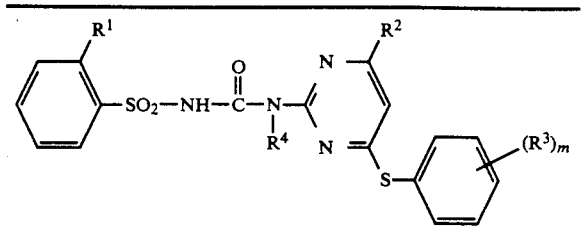

| R¹ | R⁴ | R² | (R³)ₘ |
|---|---|---|---|
| CON(CH₃)OCH₃ | H | CH₃ | 2-OCH₃ |
| CON(CH₃)OCH₃ | H | OCH₃ | 3-OCH₃ |
| CON(CH₃)OCH₃ | H | Cl | 2-OCH₃ |
| CO₂(CH₂)₂Cl | H | Cl | 2-N(CH₃)₂ |
| CO₂(CH₂)₂OCH₃ | H | Cl | 2-CN |
| CO₂(CH₂)₂OC₂H₅ | CH₃ | Cl | 2-NO₂ |
| CO₂(CH₂)₂OCF₃ | H | Cl | 2,3-Cl,Cl |
| OCH₃ | H | Cl | 2-Cl |
| OCH₃ | H | Cl | 3-NO₂ |
| OC₂H₅ | H | Cl | 4-CN |
| O(CH₂)₂Cl | H | CH₃ | 3-CH₃ |
| O(CH₂)₂F | CH₃ | CH₃ | 2-Cl,4-CF₃ |
| O(CH₂)₂OCH₃ | CH₃ | CH₃ | 2,3,5-Cl,Cl,Cl |
| O(CH₂)₂OCH₃ | CH₃ | CH₃ | 3-N(CH₃)₂ |
| O(CH₂)₂SCH₃ | CH₃ | CH₃ | 4-OCH₃ |
| O(CH₂)₂SCH₃ | CH₃ | OCH₃ | 2,4-Cl,Cl |
| O(CH₂)₂SCF₃ | CH₃ | OCH₃ | 2-OCH₃ |

TABLE C

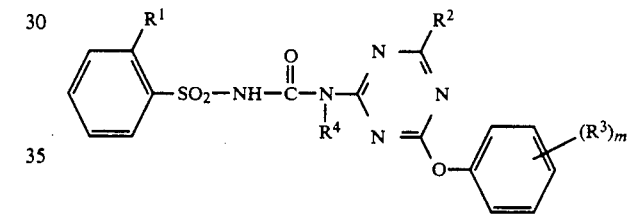

| R¹ | R⁴ | R² | (R³)ₘ |
|---|---|---|---|
| CO₂CH₃ | H | Cl | H |
| CO₂CH₃ | H | Cl | 3-CH₃ |
| CO₂CH₃ | H | Cl | 3-OCH₃ |
| CO₂CH₃ | H | Cl | 3-CF₃ |
| CO₂CH₃ | H | Cl | 2-F |
| CO₂CH₃ | H | Cl | 2-Cl |
| CO₂CH₃ | H | Cl | 3-Cl |
| CO₂CH₃ | H | Cl | 3-NO₂ |
| CO₂CH₃ | H | Cl | 4-NO₂ |
| CO₂CH₃ | H | Cl | 2-CN |
| CO₂CH₃ | H | Cl | 2,6-OCH₃,OCH₃ |
| CO₂CH₃ | H | Cl | 2,4,6-Cl,Cl,Cl |
| CO₂CH₃ | H | Cl | 2-Cl,4-CF₃ |
| CO₂CH₃ | H | Cl | 3-N(CH₃)₂ |
| CO₂CH₃ | CH₃ | Cl | H |
| CO₂CH₃ | CH₃ | Cl | 3-CH₃ |
| CO₂CH₃ | CH₃ | Cl | 3-OCH₃ |
| CO₂CH₃ | CH₃ | Cl | 3-CF₃ |
| CO₂CH₃ | CH₃ | Cl | 2-F |
| CO₂CH₃ | CH₃ | Cl | 2-Cl |
| CO₂CH₃ | CH₃ | Cl | 3-Cl |
| CO₂CH₃ | CH₃ | Cl | 3-NO₂ |
| CO₂CH₃ | CH₃ | Cl | 4-NO₂ |
| CO₂CH₃ | CH₃ | Cl | 2-CN |
| CO₂CH₃ | CH₃ | Cl | 2,6-OCH₃,OCH₃ |
| CO₂CH₃ | CH₃ | Cl | 2,4,6-Cl,Cl,Cl |
| CO₂CH₃ | CH₃ | Cl | 2-Cl,4-CF₃ |
| CO₂CH₃ | CH₃ | Cl | 3-N(CH₃)₂ |
| CO₂CH₃ | H | CH₃ | H |
| CO₂CH₃ | H | CH₃ | 3-CH₃ |
| CO₂CH₃ | H | CH₃ | 3-OCH₃ |
| CO₂CH₃ | H | CH₃ | 3-CF₃ |
| CO₂CH₃ | H | CH₃ | 2-F |
| CO₂CH₃ | H | CH₃ | 2-Cl |
| CO₂CH₃ | H | CH₃ | 3-Cl |
| CO₂CH₃ | H | CH₃ | 3-NO₂ |

TABLE C-continued

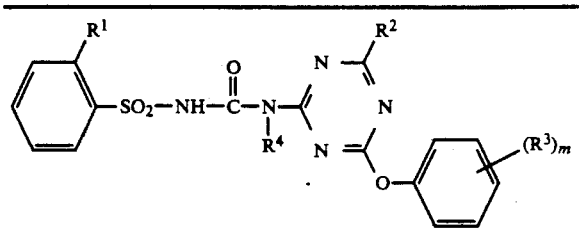

| R¹ | R⁴ | R² | (R³)ₘ |
|---|---|---|---|
| CO₂CH₃ | H | CH₃ | 4-NO₂ |
| CO₂CH₃ | H | CH₃ | 2-CN |
| CO₂CH₃ | H | CH₃ | 2,6-OCH₃,OCH₃ |
| CO₂CH₃ | H | CH₃ | 2,4,6-Cl,Cl,Cl |
| CO₂CH₃ | H | CH₃ | 2-Cl,4-CF₃ |
| CO₂CH₃ | H | CH₃ | 3-N(CH₃)₂ |
| CO₂CH₃ | H | CF₃ | H |
| CO₂CH₃ | H | CF₃ | 3-CH₃ |
| CO₂CH₃ | H | CF₃ | 3-OCH₃ |
| CO₂CH₃ | H | CF₃ | 3-CF₃ |
| CO₂CH₃ | H | CF₃ | 2-F |
| CO₂CH₃ | H | CF₃ | 2-Cl |
| CO₂CH₃ | H | CF₃ | 3-Cl |
| CO₂CH₃ | H | CF₃ | 3-NO₂ |
| CO₂CH₃ | H | CF₃ | 4-NO₂ |
| CO₂CH₃ | H | CF₃ | 2-CN |
| CO₂CH₃ | H | CF₃ | 2,6-OCH₃,OCH₃ |
| CO₂CH₃ | H | CF₃ | 2,4,6-Cl,Cl,Cl |
| CO₂CH₃ | H | CF₃ | 2-Cl,4-CF₃ |
| CO₂CH₃ | H | CF₃ | 3-N(CH₃)₂ |
| CO₂CH₃ | H | OCH₃ | H |
| CO₂CH₃ | H | OCH₃ | 3-CH₃ |
| CO₂CH₃ | H | OCH₃ | 3-OCH₃ |
| CO₂CH₃ | H | OCH₃ | 3-CF₃ |
| CO₂CH₃ | H | OCH₃ | 2-F |
| CO₂CH₃ | H | OCH₃ | 2-Cl |
| CO₂CH₃ | H | OCH₃ | 3-Cl |
| CO₂CH₃ | H | OCH₃ | 3-NO₂ |
| CO₂CH₃ | H | OCH₃ | 4-NO₂ |
| CO₂CH₃ | H | OCH₃ | 2-CN |
| CO₂CH₃ | H | OCH₃ | 2,6-OCH₃,OCH₃ |
| CO₂CH₃ | H | OCH₃ | 2,4,6-Cl,Cl,Cl |
| CO₂CH₃ | H | OCH₃ | 2-Cl,4-CF₃ |
| CO₂CH₃ | H | OCH₃ | 3-N(CH₃)₂ |
| Cl | H | Cl | H |
| Cl | H | Cl | 3-CH₃ |
| Cl | H | Cl | 3-OCH₃ |
| Cl | H | Cl | 3-CF₃ |
| Cl | H | Cl | 2-F |
| Cl | H | Cl | 2-Cl |
| Cl | H | Cl | 3-Cl |
| Cl | H | Cl | 3-NO₂ |
| Cl | H | Cl | 4-NO₂ |
| Cl | H | Cl | 2-CN |
| Cl | H | Cl | 2,6-OCH₃,OCH₃ |
| Cl | H | Cl | 2,4,6-Cl,Cl,Cl |
| Cl | H | Cl | 2-Cl,4-CF₃ |
| Cl | H | Cl | 3-N(CH₃)₂ |
| Cl | CH₃ | Cl | H |
| Cl | CH₃ | Cl | 3-CH₃ |
| Cl | CH₃ | Cl | 3-OCH₃ |
| Cl | CH₃ | Cl | 3-CF₃ |
| Cl | CH₃ | Cl | 2-F |
| Cl | CH₃ | Cl | 2-Cl |
| Cl | CH₃ | Cl | 3-Cl |
| Cl | CH₃ | Cl | 3-NO₂ |
| Cl | CH₃ | Cl | 4-NO₂ |
| Cl | CH₃ | Cl | 2-CN |
| Cl | CH₃ | Cl | 2,6-OCH₃,OCH₃ |
| Cl | CH₃ | Cl | 2,4,6-Cl,Cl,Cl |
| Cl | CH₃ | Cl | 2-Cl,4-CF₃ |
| Cl | CH₃ | Cl | 3-N(CH₃)₂ |
| Cl | H | CH₃ | H |
| Cl | H | CH₃ | 3-CH₃ |
| Cl | H | CH₃ | 3-OCH₃ |
| Cl | H | CH₃ | 3-CF₃ |
| Cl | H | CH₃ | 2-F |
| Cl | H | CH₃ | 2-Cl |
| Cl | H | CH₃ | 3-Cl |
| Cl | H | CH₃ | 3-NO₂ |

TABLE C-continued

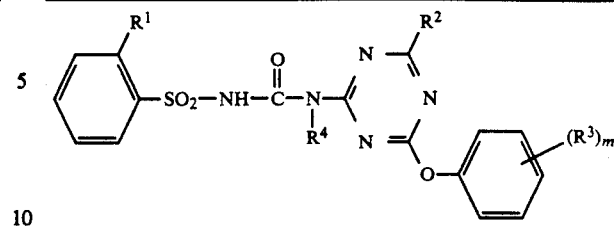

| R¹ | R⁴ | R² | (R³)ₘ |
|---|---|---|---|
| Cl | H | CH₃ | 4-NO₂ |
| Cl | H | CH₃ | 2-CN |
| Cl | H | CH₃ | 2,6-OCH₃,OCH₃ |
| Cl | H | CH₃ | 2,4,6-Cl,Cl,Cl |
| Cl | H | CH₃ | 2-Cl,4-CF₃ |
| Cl | H | CH₃ | 3-N(CH₃)₂ |
| Cl | H | CF₃ | H |
| Cl | H | CF₃ | 3-CH₃ |
| Cl | H | CF₃ | 3-OCH₃ |
| Cl | H | CF₃ | 3-CF₃ |
| Cl | H | CF₃ | 2-F |
| Cl | H | CF₃ | 2-Cl |
| Cl | H | CF₃ | 3-Cl |
| Cl | H | CF₃ | 3-NO₂ |
| Cl | H | CF₃ | 4-NO₂ |
| Cl | H | CF₃ | 2-CN |
| Cl | H | CF₃ | 2,6-OCH₃,OCH₃ |
| Cl | H | CF₃ | 2,4,6-Cl,Cl,Cl |
| Cl | H | CF₃ | 2-Cl,4-CF₃ |
| Cl | H | CF₃ | 3-N(CH₃)₂ |
| Cl | H | OCH₃ | H |
| Cl | H | OCH₃ | 3-CH₃ |
| Cl | H | OCH₃ | 3-OCH₃ |
| Cl | H | OCH₃ | 3-CF₃ |
| Cl | H | OCH₃ | 2-F |
| Cl | H | OCH₃ | 2-Cl |
| Cl | H | OCH₃ | 3-Cl |
| Cl | H | OCH₃ | 3-NO₂ |
| Cl | H | OCH₃ | 4-NO₂ |
| Cl | H | OCH₃ | 2-CN |
| Cl | H | OCH₃ | 2,6-OCH₃,OCH₃ |
| Cl | H | OCH₃ | 2,4,6-Cl,Cl,Cl |
| Cl | H | OCH₃ | 2-Cl,4-CF₃ |
| Cl | H | OCH₃ | 3-N(CH₃)₂ |

TABLE D

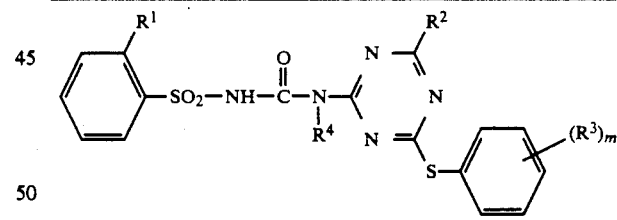

| R¹ | R⁴ | R² | (R³)ₘ |
|---|---|---|---|
| CO₂CH₃ | H | Cl | H |
| CO₂CH₃ | H | Cl | 3-CH₃ |
| CO₂CH₃ | H | Cl | 3-OCH₃ |
| CO₂CH₃ | H | Cl | 3-CF₃ |
| CO₂CH₃ | H | Cl | 2-F |
| CO₂CH₃ | H | Cl | 2-Cl |
| CO₂CH₃ | H | Cl | 3-Cl |
| CO₂CH₃ | H | Cl | 3-NO₂ |
| CO₂CH₃ | H | Cl | 4-NO₂ |
| CO₂CH₃ | H | Cl | 2-CN |
| CO₂CH₃ | H | Cl | 2,6-OCH₃,OCH₃ |
| CO₂CH₃ | H | Cl | 2,4,6-Cl,Cl,Cl |
| CO₂CH₃ | H | Cl | 2-Cl,4-CF₃ |
| CO₂CH₃ | H | Cl | 3-N(CH₃)₂ |
| CO₂CH₃ | CH₃ | Cl | H |
| CO₂CH₃ | CH₃ | Cl | 3-CH₃ |
| CO₂CH₃ | CH₃ | Cl | 3-OCH₃ |
| CO₂CH₃ | CH₃ | Cl | 3-CF₃ |
| CO₂CH₃ | CH₃ | Cl | 2-F |

TABLE D-continued

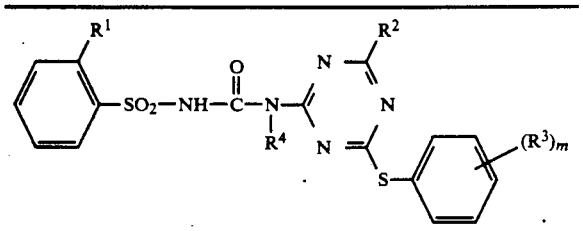

| R¹ | R⁴ | R² | (R³)ₘ |
|---|---|---|---|
| CO₂CH₃ | CH₃ | Cl | 2-Cl |
| CO₂CH₃ | CH₃ | Cl | 3-Cl |
| CO₂CH₃ | CH₃ | Cl | 3-NO₂ |
| CO₂CH₃ | CH₃ | Cl | 4-NO₂ |
| CO₂CH₃ | CH₃ | Cl | 2-CN |
| CO₂CH₃ | CH₃ | Cl | 2,6-OCH₃,OCH₃ |
| CO₂CH₃ | CH₃ | Cl | 2,4,6-Cl,Cl,Cl |
| CO₂CH₃ | CH₃ | Cl | 2-Cl,4-CF₃ |
| CO₂CH₃ | CH₃ | Cl | 3-N(CH₃)₂ |
| CO₂CH₃ | H | CH₃ | H |
| CO₂CH₃ | H | CH₃ | 3-CH₃ |
| CO₂CH₃ | H | CH₃ | 3-OCH₃ |
| CO₂CH₃ | H | CH₃ | 3-CF₃ |
| CO₂CH₃ | H | CH₃ | 2-F |
| CO₂CH₃ | H | CH₃ | 2-Cl |
| CO₂CH₃ | H | CH₃ | 3-Cl |
| CO₂CH₃ | H | CH₃ | 3-NO₂ |
| CO₂CH₃ | H | CH₃ | 4-NO₂ |
| CO₂CH₃ | H | CH₃ | 2-CN |
| CO₂CH₃ | H | CH₃ | 2,6-OCH₃,OCH₃ |
| CO₂CH₃ | H | CH₃ | 2,4,6-Cl,Cl,Cl |
| CO₂CH₃ | H | CH₃ | 2-Cl,4-CF₃ |
| CO₂CH₃ | H | CH₃ | 3-N(CH₃)₂ |
| CO₂CH₃ | H | CF₃ | H |
| CO₂CH₃ | H | CF₃ | 3-CH₃ |
| CO₂CH₃ | H | CF₃ | 3-OCH₃ |
| CO₂CH₃ | H | CF₃ | 3-CF₃ |
| CO₂CH₃ | H | CF₃ | 2-F |
| CO₂CH₃ | H | CF₃ | 2-Cl |
| CO₂CH₃ | H | CF₃ | 3-Cl |
| CO₂CH₃ | H | CF₃ | 3-NO₂ |
| CO₂CH₃ | H | CF₃ | 4-NO₂ |
| CO₂CH₃ | H | CF₃ | 2-CN |
| CO₂CH₃ | H | CF₃ | 2,6-OCH₃,OCH₃ |
| CO₂CH₃ | H | CF₃ | 2,4,6-Cl,Cl,Cl |
| CO₂CH₃ | H | CF₃ | 2-Cl,4-CF₃ |
| CO₂CH₃ | H | CF₃ | 3-N(CH₃)₂ |
| CO₂CH₃ | H | OCH₃ | H |
| CO₂CH₃ | H | OCH₃ | 3-CH₃ |
| CO₂CH₃ | H | OCH₃ | 3-OCH₃ |
| CO₂CH₃ | H | OCH₃ | 3-CF₃ |
| CO₂CH₃ | H | OCH₃ | 2-F |
| CO₂CH₃ | H | OCH₃ | 2-Cl |
| CO₂CH₃ | H | OCH₃ | 3-Cl |
| CO₂CH₃ | H | OCH₃ | 3-NO₂ |
| CO₂CH₃ | H | OCH₃ | 4-NO₂ |
| CO₂CH₃ | H | OCH₃ | 2-CN |
| CO₂CH₃ | H | OCH₃ | 2,6-OCH₃,OCH₃ |
| CO₂CH₃ | H | OCH₃ | 2,4,6-Cl,Cl,Cl |
| CO₂CH₃ | H | OCH₃ | 2-Cl,4-CF₃ |
| CO₂CH₃ | H | OCH₃ | 3-N(CH₃)₂ |
| Cl | H | Cl | H |
| Cl | H | Cl | 3-CH₃ |
| Cl | H | Cl | 3-OCH₃ |
| Cl | H | Cl | 3-CF₃ |
| Cl | H | Cl | 2-F |
| Cl | H | Cl | 2-Cl |
| Cl | H | Cl | 3-Cl |
| Cl | H | Cl | 3-NO₂ |
| Cl | H | Cl | 4-NO₂ |
| Cl | H | Cl | 2-CN |
| Cl | H | Cl | 2,6-OCH₃,OCH₃ |
| Cl | H | Cl | 2,4,6-Cl,Cl,Cl |
| Cl | H | Cl | 2-Cl,4-CF₃ |
| Cl | H | Cl | 3-N(CH₃)₂ |
| Cl | CH₃ | Cl | H |
| Cl | CH₃ | Cl | 3-CH₃ |
| Cl | CH₃ | Cl | 3-OCH₃ |
| Cl | CH₃ | Cl | 3-CF₃ |
| Cl | CH₃ | Cl | 2-F |

TABLE D-continued

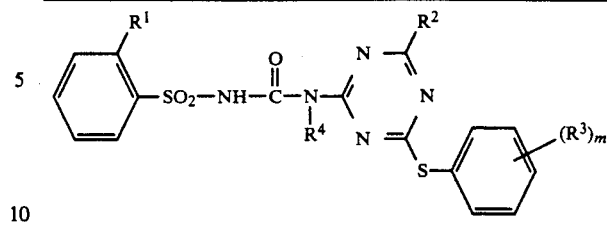

| R¹ | R⁴ | R² | (R³)ₘ |
|---|---|---|---|
| Cl | CH₃ | Cl | 2-Cl |
| Cl | CH₃ | Cl | 3-Cl |
| Cl | CH₃ | Cl | 3-NO₂ |
| Cl | CH₃ | Cl | 4-NO₂ |
| Cl | CH₃ | Cl | 2-CN |
| Cl | CH₃ | Cl | 2,6-OCH₃,OCH₃ |
| Cl | CH₃ | Cl | 2,4,6-Cl,Cl,Cl |
| Cl | CH₃ | Cl | 2-Cl,4-CF₃ |
| Cl | CH₃ | Cl | 3-N(CH₃)₂ |
| Cl | H | CH₃ | H |
| Cl | H | CH₃ | 3-CH₃ |
| Cl | H | CH₃ | 3-OCH₃ |
| Cl | H | CH₃ | 3-CF₃ |
| Cl | H | CH₃ | 2-F |
| Cl | H | CH₃ | 2-Cl |
| Cl | H | CH₃ | 3-Cl |
| Cl | H | CH₃ | 3-NO₂ |
| Cl | H | CH₃ | 4-NO₂ |
| Cl | H | CH₃ | 2-CN |
| Cl | H | CH₃ | 2,6-OCH₃,OCH₃ |
| Cl | H | CH₃ | 2,4,6-Cl,Cl,Cl |
| Cl | H | CH₃ | 2-Cl,4-CF₃ |
| Cl | H | CH₃ | 3-N(CH₃)₂ |
| Cl | H | CF₃ | H |
| Cl | H | CF₃ | 3-CH₃ |
| Cl | H | CF₃ | 3-OCH₃ |
| Cl | H | CF₃ | 3-CF₃ |
| Cl | H | CF₃ | 2-F |
| Cl | H | CF₃ | 2-Cl |
| Cl | H | CF₃ | 3-Cl |
| Cl | H | CF₃ | 3-NO₂ |
| Cl | H | CF₃ | 4-NO₂ |
| Cl | H | CF₃ | 2-CN |
| Cl | H | CF₃ | 2,6-OCH₃,OCH₃ |
| Cl | H | CF₃ | 2,4,6-Cl,Cl,Cl |
| Cl | H | CF₃ | 2-Cl,4-CF₃ |
| Cl | H | CF₃ | 3-N(CH₃)₂ |
| Cl | H | OCH₃ | H |
| Cl | H | OCH₃ | 3-CH₃ |
| Cl | H | OCH₃ | 3-OCH₃ |
| Cl | H | OCH₃ | 3-CF₃ |
| Cl | H | OCH₃ | 2-F |
| Cl | H | OCH₃ | 2-Cl |
| Cl | H | OCH₃ | 3-Cl |
| Cl | H | OCH₃ | 3-NO₂ |
| Cl | H | OCH₃ | 4-NO₂ |
| Cl | H | OCH₃ | 2-CN |
| Cl | H | OCH₃ | 2,6-OCH₃,OCH₃ |
| Cl | H | OCH₃ | 2,4,6-Cl,Cl,Cl |
| Cl | H | OCH₃ | 2-Cl,4-CF₃ |
| Cl | H | OCH₃ | 3-N(CH₃)₂ |

The substituted sulfonylureas I, and herbicidal agents containing them, may be applied for instance in the form of directly sprayable solutions, powders, suspensions (including high-percentage aqueous, oily or other suspensions), dispersion, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenese and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredients, wetting agent, adherent, emulsifying or dispersing agent and possibly solvent or oil.

Examples of surfactants are: alkali metal, alkaline earth metal and ammonium salts of aromatic sulfonic acids, e.g., lignisulfonic acid, phenosulfonic acid, naphthalenesulfonic acid and dibutylnaphthalene-sulfonic acid, and of fatty acids, alkyl and alkylaryl suflonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylarly polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose. Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 1.002 is mixed with 10 parts by weight of N-methyl-alpha-pyrrolidone. A mixture is obtained which is suitable for application in the form of very fine drops.

II. 20 parts by weight of compound no. 1.003 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.006 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil, By pouring the solution into 100,000 parts by weight of water and finely distributing it therein, an aqueous dispersion is obtained containing 0.02% by weight of the active ingredient.

IV. 20 parts by weight of compound no. 1.002 is dissolved in a mixture consisting of 25 parts by weight of cyclohexanone, 65 parts by weight of a mineral oil fraction having a boiling point between 210 and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 5.005 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.006 is intimately mixed with 97 parts by weight of particulate kaolin. A dust is obtained containing 3% by weight of the active ingredient.

VII. 30 parts by weight of compound no. 5.005 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 6.003 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are is possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

The sulfonylureas of the general formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

Cost-intensive pruning can be reduced in fruit and other trees and shrubs as a result of the use of growth regulators.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts being. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is preventive measure against increased susceptibility to freeze injury and—because of the relatively low leaf or plant mass - attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The sulfonylureas of the formula I may raise the yield by influencing plant metabolism or by promoting or inhibiting vegetative and/or generative plant growth.

C. It is also possible with sulfonylureas I to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with the sulfonylureas I. This is particularly important for plants growing in agricultural areas which are expensive to irrigate, e.g., in arid or semi-arid areas. Irrigation frequency can be reduce by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance of compounds I by crop plants, the application rate may vary within wide limits. When the active ingredients are used for treating seed, amounts of from 0.001 to 50, and preferably from 0.01 to 10, g are generally required. For foliage and soil treatment, amounts of from 0.01 to 10, and preferably from 0.01 to 5, kg/ha are generally considered to be sufficient.

In view of the number of application methods possible, the compounds according to the invention, or agents containing them, may be used in a further large number of crops for removing unwanted plants.

To increase the spectrum of action and to achieve synergistic effects, the sulfonylureas of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxyphenylpropionic acids and derivatives thereof, etc.

It may also be useful to apply the novel compounds of the formula I, either along or in combination while other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

The directions given in the examples below were used, after appropriate modifications to the starting compounds, to obtain further compounds of the formula I.

SYNTHESIS EXAMPLES

1. Manufacture of intermediates III

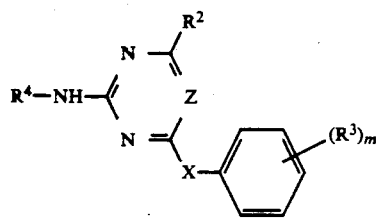

1.1
2-Amino-6-methyl-4-(2-cyano-1-phenoxy)-pyrimidine

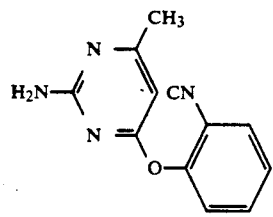

AT 60° C. and while stirring, 4.7 g, of potassium hydroxide (84 mmol) was added to 10.0 g (84 mmol) of o-hydroxybenzonitrile in 100 ml of methanol until a clear solution formed. The reaction mixture was subsequently evaporated down. The residue was taken up in 100 ml of N-methyl-2-pyrrolidone, 12,0 g (84 mmol) of 2-amino-4-chloro-6-methylpyrimidine was added and the mixture stirred for 6 hours at 140° C. After cooling, the reaction mixture was poured, at 25° C., onto ice and the precipitate was isolated.

There was obtained 90% of theory of the product; m.p. 163-165° C.

1.2
2-Amino-4-chloro-6-(2,4-dichloro-1-phenoxy)-1,3,5-triazine

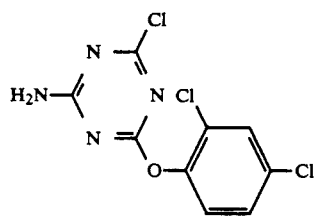

7.9 g (48.5 mmol) of 2,4-dichlorophenol and 8.0 g (48.5 mmol) of 2-amino-4,6-dichloro-1,3,5-triazine were added to a solution of 5.1 g (48.5 mmol) of sodium carbonate and 150 ml of water, and the mixture was stirred for 4 hours at 50° C. After the mixture had cooled to 25° C. the precipitate was filtered off and dried; there was obtained 92% of theory of the product.

$^1$H NMR data (DMSO, int. TMS, 250 MHz): δ8.32 (broad; NH), 8.24 (broad; NH); 7.83 7.53 ppm (multiplets, aromatic protons).

The compounds given in the table blew were obtained analogously.

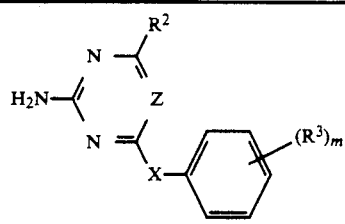

| No. | $R^2$ | Z | X | $(R^3)_m$ | Melting point (°C.) or the $^1$H NMR shift (δ/ppm) of the H(5) proton on the pyridine ring (vs TMS) |
|---|---|---|---|---|---|
| 1.3 | Cl | CH | O | 2-OCH$_3$ | 188-190 |
| 1.4 | Cl | CH | O | 3-OCH$_3$ | 140-142 |
| 1.5 | Cl | CH | O | 4-OCH$_3$ | 6.13 (d$_6$-DMSO) |
| 1.6 | Cl | CH | O | 2-Cl | 155-158 |
| 1.7 | Cl | CH | O | 3-Cl | 140-141 |
| 1.8 | Cl | CH | O | 2-NO$_2$ | 6.48 (d$_6$-DMSO) |
| 1.9 | Cl | CH | O | 3-NO$_2$ | 6.40 (d$_6$-DMSO) |
| 1.10 | Cl | CH | O | 4-NO$_2$ | 6.43 (d$_6$-DMSO) |
| 1.11 | Cl | CH | O | 2-CN | 6.53 (d$_6$-DMSO) |
| 1.12 | Cl | CH | O | 3-CN | 204-205 |
| 1.13 | Cl | CH | O | 4-CN | 6.37 (d$_6$-DMSO) |
| 1.14 | Cl | CH | O | 2-F | 160-165 |
| 1.15 | Cl | CH | O | 3-CF$_3$ | 6.25 (CDCl$_3$) |
| 1.16 | Cl | CH | O | 2-OCH$_3$, 6-OCH$_3$ | 188-190 |
| 1.17 | Cl | CH | O | 2-Cl, 4-Cl, 6-Cl | 6.36 (d$_6$-DMSO) |
| 1.18 | CH$_3$ | CH | O | 3-OCH$_3$ | 194-195 |
| 1.19 | CH$_3$ | CH | O | 4-OCH$_3$ | 5.92 (CDCl$_3$) |
| 1.20 | CH$_3$ | CH | O | 3-CN | 119-120 |
| 1.21 | CH$_3$ | CH | O | 4-CN | 215-217 |
| 1.22 | CH$_3$ | CH | O | 3-CF$_3$ | 6.07 (CDCl$_3$) |
| 1.23 | CH$_3$ | CH | O | 2-F | 6.13 (d$_6$-DMSO) |
| 1.24 | CH$_3$ | CH | O | 2-NO$_2$ | 6.20 (d$_6$-DMSO) |

-continued

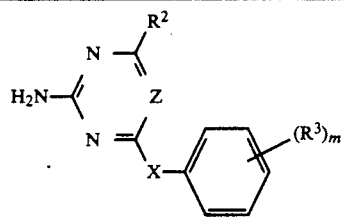

| No. | R² | Z | X | (R³)ₘ | Melting point (°C.) or the ¹H NMR shift (δ/ppm) of the H(5) proton on the pyridine ring (vs TMS) |
|---|---|---|---|---|---|
| 1.25 | CH₃ | CH | O | 3-NO₂ | 179–180 |
| 1.26 | CH₃ | CH | O | 4-NO₂ | 219–220 |
| 1.27 | CH₃ | CH | O | 2-Cl | 183–184 |
| 1.28 | CH₃ | CH | O | 3-Cl | 159–160 |
| 1.29 | CH₃ | CH | O | 4-Cl | 219–220 |
| 1.30 | CH₃ | CH | O | 2-OCH₃, 6-OCH₃ | 168–173 |
| 1.31 | CH₃ | CH | O | 2-Cl, 4-Cl, 6-Cl | 130–131 |
| 1.32 | OCH₃ | CH | O | 4-OCH₃ | 5.36 (CDCl₃) |
| 1.33 | Cl | CH | S | 2-Cl | 6.04 (CDCl₃) |
| 1.34 | Cl | CH | S | 2-OCH₃ | 5.74 (d₆-DMSO) |
| 1.35 | Cl | N | O | 2-OCH₃ | 230 |
| 1.36 | Cl | N | O | 3-OCH₃ | 3.76 [(OCH₃)d₆-DMSO] |
| 1.37 | Cl | N | O | 4-OCH₃ | 230 |
| 1.38 | Cl | N | O | 2-Cl | 220–223 |
| 1.39 | Cl | N | O | 3-Cl | 227–228 |
| 1.40 | Cl | N | O | 4-Cl | >230 |
| 1.41 | Cl | N | O | 2-CN | >230 |
| 1.42 | Cl | N | O | 3-CN | >230 |
| 1.43 | Cl | N | O | 4-CN | >230 |
| 1.44 | Cl | CH | O | 2-Cl, 4-Cl | 6,43 (d₆-DMSO) |
| 1.45 | Cl | CH | O | 2-Cl, 4-CF₃ | 104–106 |
| 1.46 | Cl | CH | O | 3-N(CH₃)₂ | 194–204 |
| 1.47 | CH₃ | CH | O | 3-N(CH₃)₂ | 232–235 |
| 1.48 | OCH₃ | CH | O | 2-Cl | 5.53 (d⁶-DMSO) |
| 1.49 | OCH₃ | CH | O | 3-Cl | 112–115 |
| 1.50 | OCH₃ | CH | O | 4-Cl | 105–108 |
| 1.51 | OCH₃ | CH | O | 2-OCH₃ | 104–106 |
| 1.52 | OCH₃ | CH | O | 3-OCH₃ | 85–88 |
| 1.53 | CH₃ | CH | S | 4-OCH₃ | 200–203 |
| 1.54 | F | CH | O | 2-OCH₃ | 166 |
| 1.55 | F | CH | O | 3-OCH₃ | 115–116 |
| 1.56 | F | CH | O | 4-OCH₃ | 195–197 |
| 1.57 | OCH₃ | CH | O | 3-OCH₃, 4-OCH₃, 5-OCH₃ | 120–122 |
| 1.58 | OCH₃ | CH | O | 4-OC₂H₅ | 145–146 |
| 1.59 | OC₂H₅ | CH | O | 2-OCH₃ | 130–131 |
| 1.60 | OC₂H₅ | CH | O | 4-OC₂H₅ | 127 |
| 1.61 | CF₃ | CH | O | 2-OCH₃ | 168–170 |
| 1.62 | CF₃ | CH | O | 3-OCH₃ | 127–129 |
| 1.63 | OC₂H₅ | CH | O | 3-OCH₃ | 82 |
| 1.64 | OCH₃ | CH | O | 3-OCH₃, 5-OCH₃ | 85–86 |
| 1.65 | OCH₃ | CH | O | 3-OCH₃, 4-OCH₃ | 148–149 |
| 1.66 | CF₃ | CH | O | 3-N(CH₃)₂ | 115–116 |
| 1.67 | OC₂H₅ | CH | O | 3-N(CH₃)₂ | 122–124 |
| 1.68 | OCH₃ | CH | O | 2-OCH₃, 3-OCH₃ | 5,42 (CDCl₃) |
| 1.69 | OCH₃ | CH | O | 3,4-(OCH₂O) | 135–140 |
| 1.70 | OCH₃ | CH | O | 2-OC₂H₅ | 5,40 (CDCl₃) |
| 1.71 | OCH₃ | CH | O | 2-OCH₃, 4-CH₃ | 5,38 (CDCl₃) |
| 1.72 | OCH₃ | CH | O | 2-OCH₃, 4-(E)-CH=CH—CH₃ | 5,39 (CDCl₃) |
| 1.73 | OCH₃ | CH | O | 2-OCH₂C₆H₅ | 75–78 |
| 1.74 | OCH₃ | CH | O | 4-OCH₂C₆H₅ | 152–155 |
| 1.75 | Cl | CH | O | 2-CO₂CH₃ | 200–201 |
| 1.76 | OCH₃ | CH | O | 2-t.-C₄H₉, 4-OCH₃ | 135–138 |
| 1.77 | OCH₃ | CH | O | 2-N⟨  ⟩ | 117–125 |
| 1.78 | OCH₃ | CH | O | 2-N⟨  ⟩O | 174–180 |
| 1.79 | OCH₃ | CH | O | 3-CH₃, 4-SCH₃ | 96–98 |
| 1.80 | OCH₃ | CH | O | 2-Cl, 4-OCH₃ | 5,45 (d₆-DMSO) |
| 1.81 | OCH₃ | CH | O | 4-SCH₃ | 5,43 (d₆-DMSO) |

-continued

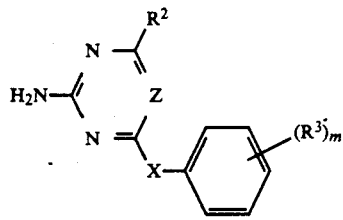

| No. | R² | Z | X | (R³)ₘ | Melting point (°C.) or the ¹H NMR shift (δ/ppm) of the H(5) proton on the pyridine ring (vs TMS) |
|---|---|---|---|---|---|
| 1.82 | OCH₃ | CH | O | 2-CH₃, 4-SCH₃ | 5.39 (CDCl₃) |
| 1.83 | OCH₃ | CH | O | 2-OCH₃, 4-C(O)CH₃ | 5.49 (CDCl₃) |
| 1.84 | OCH₃ | CH | O | 2-OC₂H₅, 4-Cl | 5.42 (d₆-DMSO) |

2. Manufacture of the intermediates V

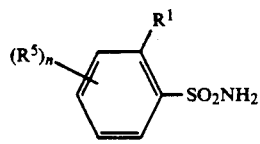

2.1 Methyl 2-aminosulfonyl-6-chlorobenzoate

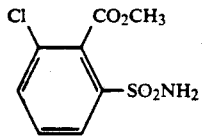

a) 4-Chloro-1,2-benzisothiazol-3-one-1,1-dioxide 504 g (2.02 mol) of methyl 6-chloro-2-amnosulfonylbenzoate was added in portions to a solution of 80 g (2.0 mol) of sodium hydroxide in 2.5 liters of water; the temperature rose from 25° C. to 50° C. After 30 minutes at this temperature, the mixture was cooled to 25° C. and extracted with methyl tert-butyl ether, and the aqueous phase was stirred into 2 N hydrochloric acid. The precipitate was isolated, washed with water and dried. There was obtained 330 g (75.8% of theory) of the title compound, m.p.: 210–212° C.

b) Methyl 2-aminosulfonyl-6-chlorobenzoate 93 g (0.43 mmol) of 4-chloro-1,2-benzisothiazol-3-one-1,1-dioxide was suspended in 0.8 liter of methanol; while gassing with hydrogen chloride the mixture was refluxed for 3 hours. After cooling to 20° C., suction filtration and drying, there was obtained 56% of theory of the title compound of m.p. 152–153° C. By evaporating down the filtrate under reduced pressure and triturating the residue with methyl tert-butyl ether, renewed filtration and drying there was obtained 39% of theory of a second fraction of this compound of m.p. 144–149° C.

For instance the following compounds were obtained analogously:

| | Cl / CO₂R / SO₂NH₂ | F / CO₂R / SO₂NH₂ |
|---|---|---|
| R | mp (°C.) | mp (°C.) |
| C₂H₅ | 97–101 | 129–131 |
| n-C₃H₇ | 111–113 | 104–107 |
| i-C₃H₇ | 145–147 | 84–87 |

2.2 Methyl 2-aminosulfonyl-6-fluorobenzoate

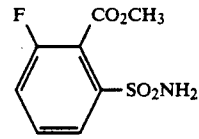

a) Methyl 2-chlorosulfonyl-6-fluorobenzoate

At 5° C. and while stirring, 108 g (0.64 mol) of methyl 6-fluoroanthranilate and 45 g (0.65 mol) of sodium nitrite in 106 ml of water were added separately but simultaneously over a period of 1 hour in such a manner to 250 ml of concentrated hydrochloric acid that the ester component was in an excess. After the reaction mixture had been stirred for 20 minutes at 5 to 8° C., it was poured all at once into a prepared solution of 53 g of sulfur dioxide, 1.7 g of copper (II) chloride in a small amount of water and 200 ml of 1,2-dichloroethane, and stirred for a further 10 minutes. The mixture was heated slowly to 50° C. and stirred for ninety minutes while passing in 46 g of sulfur dioxide. The mixture was then cooled to 20° C. and 5.5 g of chlorine was passed in over a 20-minute period while stirring. The organic phase was then separated, washed with water and dried. There was obtained 65% of theory of the title compound as a brownish oil.

b) Methyl 2-aminosulfonyl-6-fluorobenzoate

AT 20 to 28° C. and while stirring, 42.5 g of ammonia was gassed into mixture of 252.6 g (1 mol) of methyl 2-chlorosulfonyl-6-fluorobenzoate in 700 ml of anhydrous tetrahydrofuran. After the mixture had been stirred for an hour at 25° C., the precipitate was filtered off, dissolved in water, and extracted once with ethyl acetate. Acidification of the aqueous phase with concentrated hydrochloric acid gave 4% of theory of 4-fluoro-1,2-benzisothiazol-3-one-1,1-dioxide of m.p. 210 to 212° C.

The tetrahydrofuran filtrate was concentrated, washed with water, filtered, washed with diethyl ether, filtered again and dried. There was obtained 80% of theory of the title compound; m.p. 155 to 159° C.

3. Manufacture of active ingredients I 3.1 Methyl 2-[[[4-chloro-6-[(3-methoxy)-1-phenoxy]pyrimidin-2-yl]-aminocarbonyl]aminosulfonyl]-benzoate

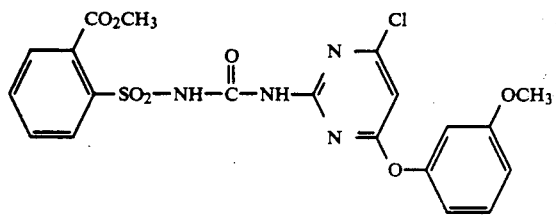

At 25° C., a solution of 6.9 g (29 mmol) of methyl 2-isocyanatosulfonyl benzoate in 40 ml of acetonitrile was added to a suspension of 6.0 g (24 mmol) of 2-amino-4-chloro-6-[(3-methoxy)-1-phenoxy]pyrimidine (1.4) in 70 ml of acetonitrile. After the mixture had been stirred for 8 hours at 70° C. 300 ml of methylene chloride was added and the mixture was washed, dried and evaporated down at 25° C. The crude product obtained was recrystallized from toluene/isopropanol and washed with diethyl ether. There was obtained 28% of theory of the title compound; m.p. 152-154° C. (active ingredient example 1.003). The yield can be increased by further processing of the mother liquor and the wash phase.

3.2 Methyl 2-[[[4-chloro-6-(3-chloro-1-phenoxy)pyrimidin-2-yl]aminocarbonyl]-aminosulfonyl]benzoate

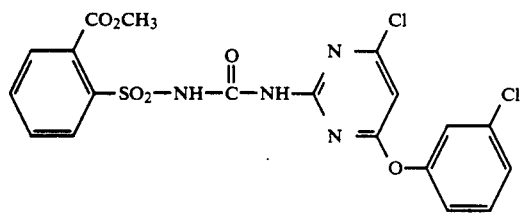

At room temperature, 7.2 g (30 mmol) of methyl 2-isocyanatosulfonylbenzoate was added to a suspension of 7.0 g (27 mmol) of 2-amino-4-chloro-6-(3-chloro-1-phenoxy)pyrimidine (1.7) in 80 ml of acetonitrile and the mixture was stirred for 2 hours at 70° C. After the mixture had been cooled to 25° C., a precipitate was obtained which was filtered off and washed crystallization from ethyl acetate gave 38% of theory of the title compound; m.p. 164-165° C. (active ingredient example 1.006). The yield can be increased by further processing of the mother liquor and the wash phase.

3.3 1-Chloro-2-[[[4-chloro-6-(2,4-dichloro-1-phenoxy)-pyrimidin-2-yl]-aminocarbonyl]aminosulfonyl]benzene

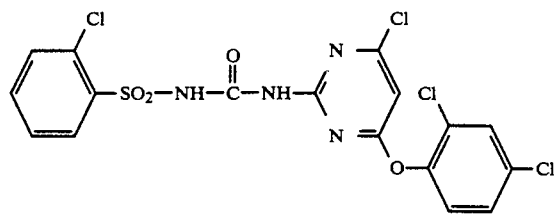

AT 25° C., 4.9 g (23 mmol) of 1-chloro-2-isocyanatosulfonylbenzene was added to a suspension of 6.0 g (21 mmol) of 2-amino-4-chloro-6-(2,4-dichloro-1-phenoxy)pyrimidine (1.44) in 70 ml of ???. After refluxing for 5 hours and cooling to 25° C., the product precipitated out. Washing and drying gave 70% of theory of the title compound; m.p. 222-223° C. (active ingredient example 2.012).

3.4 1-Chloro-2-[[[4-[(3-methoxy)-1-phenoxy]-6-methylpyridin-2-yl]aminocarbonyl]-aminosulfonyl]benzene

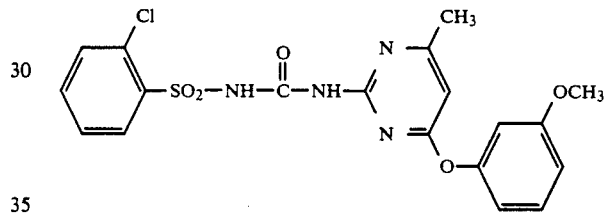

At 50° C., 3.5 g (16.6 mmol) of o-chlorobenzenesulfonyl isocyanate was added to a suspension of 3.6 g (11.2 mmol) of 1-amino-4-[(3-methoxy-1-phenoxy)]-6-methylpyrimidine (1.18) in 50 ml of acetonitrile. After the homogeneous solution had been evaporated down to b 5 ml, the product crystallized. Recrystallization with diethyl ether gave 4.8 g (95% of theory) of the title compound; m.p. 156-158° C. (active ingredient example 4.001).

3.5 1-Chloro-2-[[[4-chloro-6-(4-chloro-1-phenoxy)-1,3,5-triazin-2-yl]-aminocarbonyl]aminosulfonyl]-benzene

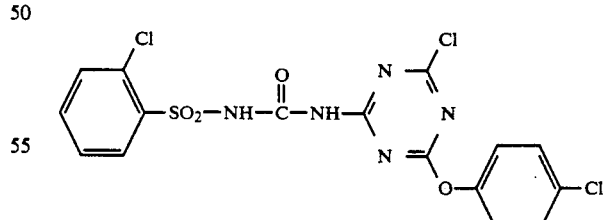

A spatula tip of 1,4-diaza(2,2,2)bocyclooctane [DABCO] and 4.2 g (19.3 mmol) of o-chlorobenzenesulfonyl isocyante were added to a suspension of 4.0 g (15.6 mmol) of 2-amino-4-chloro-6-(4-chloro-1-phenoxy)-1,3,5-triazine (1.40) in 40 ml of acetonitrile, and the mixture was refluxed for 17 hours. After the mixture had cooled it was filtered, and the product was washed with a small amount of acetonitrile and dried. There was obtained 36% of theory of the title compound; m.p.

187-190° C. (active ingredient example 9.006). The yield can be increased by further processing of the mother liquor and the wash phase.

The compounds given in Tables 1-12 were synthesized analogously to the manufacturing directions described above.

TABLE 1

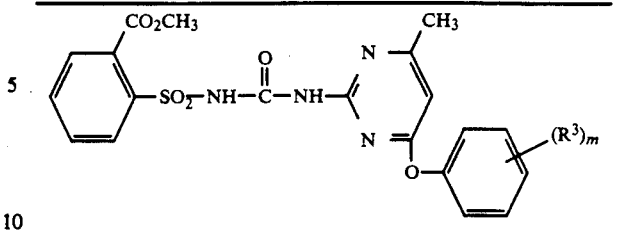

| No. | $(R^3)_m$ | Melting point (°C.) |
|---|---|---|
| 1.001 | H | 145-147 |
| 1.002 | 2-OCH$_3$ | 179-181 |
| 1.003 | 3-OCH$_3$ | 152-154 |
| 1.004 | 4-OCH$_3$ | 170-175 |
| 1.005 | 2-Cl | 175-177 |
| 1.006 | 3-Cl | 164-165 |
| 1.007 | 4-Cl | 175-180 |
| 1.008 | 2-NO$_2$ | 142-148 |
| 1.009 | 3-NO$_2$ | 200-205 |
| 1.010 | 4-NO$_2$ | 213-215 |
| 1.011 | 2-CN | 138-140 |
| 1.012 | 3-CN | 157-165 |
| 1.013 | 4-CN | 208-211 |
| 1.014 | 2-F | 133-138 |
| 1.015 | 3-CF$_3$ | 198-202 |
| 1.016 | 2-OCH$_3$, 6-OCH$_3$ | 120 |
| 1.017 | 2-Cl, 4-Cl, 6-Cl | 210-213 |
| 1.018 | 3-N(CH$_3$)$_2$ | 165-170 |
| 1.019 | 2-Cl, 4-CF$_3$ | 72-75 |
| 1.020 | 2-CO$_2$CH$_3$ | 167-170 |

TABLE 2

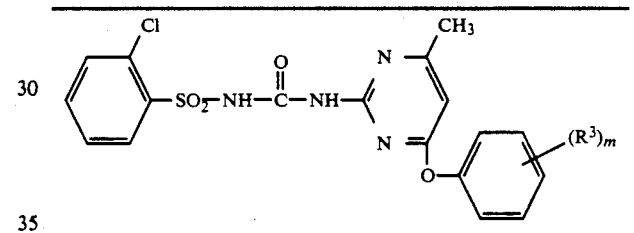

| No. | $(R^3)_m$ | Melting point (°C.) |
|---|---|---|
| 2.001 | 2-Cl | 183-185 |
| 2.002 | 3-Cl | 180-185 |
| 2.003 | 4-Cl | 211-216 |
| 2.004 | 2-NO$_2$ | 207-211 |
| 2.005 | 3-NO$_2$ | 183-188 |
| 2.006 | 4-NO$_2$ | 210-215 |
| 2.007 | 2-CN | 181-187 |
| 2.008 | 3-CN | 172-176 |
| 2.009 | 4-CN | 188-191 |
| 2.010 | 2-F | 175-178 |
| 2.011 | 4-OCH$_3$ | 159-163 |
| 2.012 | 2-Cl, 4-Cl | 222-223 |
| 2.013 | 2-OCH$_3$, 6-OCH$_3$ | 98 |
| 2.014 | 2-Cl, 4-Cl, 6-Cl | 212-214 |
| 2.015 | 2-Cl, 4-CF$_3$ | 213-215 |
| 2.016 | 3-N(CH$_3$)$_2$ | 150-155 |

TABLE 3

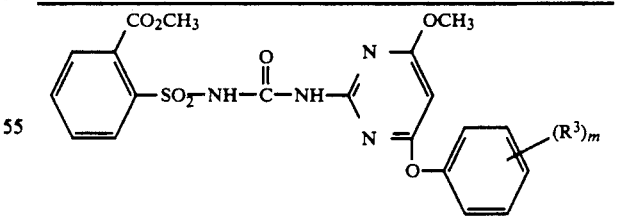

| No. | $(R^3)_m$ | Melting point (°C.) |
|---|---|---|
| 3.001 | 2-OCH$_3$ | 158-162 |
| 3.002 | 3-OCH$_3$ | 104-107 |
| 3.003 | 2-CN | 157-159 |
| 3.004 | 3-CN | 167-168 |
| 3.005 | 4-CN | 193-195 |
| 3.006 | 2-OCH$_3$, 6-OCH$_3$ | 195-197 |
| 3.007 | 2-NO$_2$ | 179-180 |
| 3.008 | 3-NO$_2$ | 184-185 |
| 3.009 | 4-NO$_2$ | 193-196 |
| 3.010 | 3-CF$_3$ | 153-156 |
| 3.011 | 3-Cl | 150-151 |
| 3.012 | 4-Cl | 193-194 |
| 3.013 | 2-F | 152-154 |
| 3.014 | 3-N(CH$_3$)$_2$ | 177-180 |
| 3.015 | 2-Cl | 148-150 |

TABLE 4

| No. | $(R^3)_m$ | Melting point (°C.) |
|---|---|---|
| 4.001 | 3-OCH$_3$ | 156-158 |
| 4.002 | 2-OCH$_3$, 6-OCH$_3$ | 199-203 |
| 4.003 | 2-F | 171-173 |
| 4.004 | 2-CN | 190-195 |
| 4.005 | 3-CN | 206-208 |
| 4.006 | 4-CN | 200-202 |
| 4.007 | 2-Cl | 188-190 |
| 4.008 | 3-Cl | 172-173 |
| 4.009 | 4-Cl | 192-193 |
| 4.010 | 2-NO$_2$ | 204-205 |
| 4.011 | 3-NO$_2$ | 196-198 |
| 4.012 | 3-CF$_3$ | 167-168 |
| 4.013 | 3-N(CH$_3$)$_2$ | 85-90 |

TABLE 5

| No. | $(R^3)_m$ | Melting point (°C.) |
|---|---|---|
| 5.001 | 4-OCH$_3$ | 146-148 |
| 5.002 | 2-Cl | 145-150 |
| 5.003 | 3-Cl | 146-150 |
| 5.004 | 4-Cl | 156-160 |
| 5.005 | 2-OCH$_3$ | 104-108 |
| 5.006 | 3-OCH$_3$ | 148-152 |
| 5.007 | 2-OCH$_2$CH$_3$ | 177-180 |
| 5.008 | 4-OCH$_2$CH$_3$ | 152 |
| 5.009 | 2-OCH$_3$, 4-CH$_3$ | 167 |
| 5.010 | 3,4-(OCH$_3$)$_2$ | 154-155 |

TABLE 5-continued

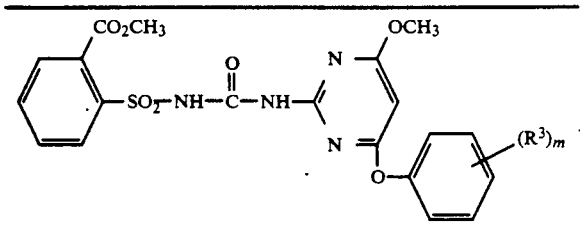

| No. | $(R^3)_m$ | Melting point (°C.) |
|---|---|---|
| 5.011 | 2-OCH₃, 4-(E)—CH=CHCH₃ | 173–175 |
| 5.012 | 2,3-(OCH₃)₂ | 155 |
| 5.013 | 3,4,5-(OCH₃)₃ | 183–184 |
| 5.014 | 3,5-(OCH₃)₂ | 177–178 |
| 5.015 | 3,4-(OCH₂O) | 180–183 |
| 5.016 | 2-t.-C₄H₉, 4-OCH₃ | 179–182 |
| 5.017 | 4-OCH₂C₆H₅ | 145–146 |
| 5.018 | 2-OCH₂C₆H₅ | 95–100 |
| 5.019 | 2-N(piperidinyl) | 163–164 |
| 5.020 | 2-N(morpholinyl) | 196–202 |
| 5.021 | 3-CH₃, 4-CH₃ | 176–178 |
| 5.022 | 4-SCH₃ | 116–120 |
| 5.023 | 2-CH₃, 4-SCH₃ | 177–179 |
| 5.024 | 2-Cl, 4-OCH₃ | 180 |
| 5.025 | 2-OCH₃, 4-C(O)CH₃ | 114–116 |
| 5.026 | 2-OC₂H₅4-Cl | 154–158 |

TABLE 6

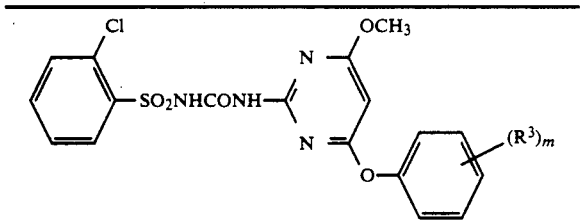

| No. | $(R^3)_m$ | Melting point (°C.) |
|---|---|---|
| 6.001 | 2-Cl | 164–170 |
| 6.002 | 3-Cl | 123–125 |
| 6.003 | 2-OCH₃ | 95–100 |
| 6.004 | 3-OCH₃ | 75–80 |
| 6.005 | 4-Cl | 177–182 |
| 6.006 | 3,4-(OCH₂O) | 124–134 |
| 6.007 | 2-t.-C₄H₉, 4-OCH₃ | 183–187 |
| 6.008 | 4-OCH₂C₆H₅ | 145–146 |
| 6.009 | 2-OCH₂C₆H₅ | 162 |
| 6.010 | 2-N(piperidinyl) | 173–177 |
| 6.011 | 3-CH₃, 4-SCH₃ | 163–165 |
| 6.012 | 2-Cl, 4-OCH₃ | 188 |
| 6.013 | 4-SCH₃ | 145–146 |
| 6.014 | 2-CH₃, 4-SCH₃ | 179–184 |
| 6.015 | 2-OCH₂CH₃, 4-Cl | 161–162 |

TABLE 7

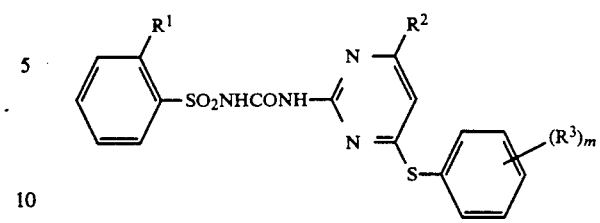

| No. | $R^1$ | $R^2$ | $(R^3)_m$ | Melting point (°C.) |
|---|---|---|---|---|
| 7.001 | CO₂CH₃ | Cl | 2-OCH₃ | 146–150 |
| 7.002 | CO₂CH₃ | Cl | 2-Cl | 185–188 |
| 7.003 | CO₂CH₃ | CH₃ | 4-OCH₃ | 193 |
| 7.004 | Cl | Cl | 2-Cl | 200–204 |
| 7.005 | Cl | Cl | 2-OCH₃ | 123–127 |
| 7.006 | Cl | CH₃ | 4-OCH₃ | 207–208 |

TABLE 8

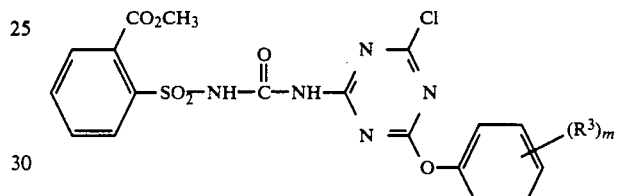

| No. | $(R^3)_m$ | Melting point (°C.) |
|---|---|---|
| 8.001 | 2-OCH₃ | 184–187 |
| 8.002 | 3-OCH₃ | 162–165 |
| 8.003 | 4-OCH₃ | 210–212 |
| 8.004 | 2-Cl | 152–156 |
| 8.005 | 3-Cl | 176–179 |
| 8.006 | 4-Cl | 165–170 |
| 8.007 | 4-CN | 168–170 |
| 8.008 | 2-Cl, 4-Cl | 173–175 |

TABLE 9

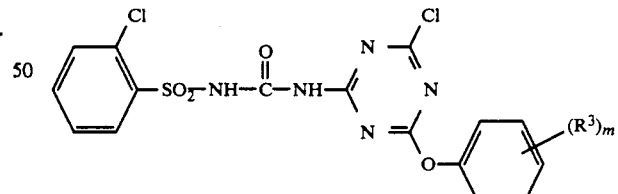

| No. | $(R^3)_m$ | Melting point (°C.) |
|---|---|---|
| 9.001 | 2-OCH₃ | 173–178 |
| 9.002 | 3-OCH₃ | 159–162 |
| 9.003 | 4-OCH₃ | 162–167 |
| 9.004 | 2-Cl | 189–193 |
| 9.005 | 3-Cl | 165–169 |
| 9.006 | 4-Cl | 187–190 |
| 9.007 | 2-CN | 174–176 |
| 9.008 | 3-CN | 186–188 |

TABLE 10

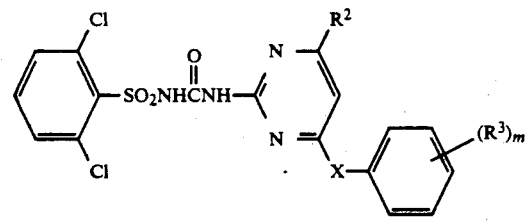

| No. | $R^2$ | X | $(R^3)_m$ | Melting point (°C.) |
|---|---|---|---|---|
| 10.001 | Cl | S | 2-OCH$_3$ | 209-211 |
| 10.002 | Cl | O | 4-Cl | >230 |
| 10.003 | Cl | O | 3-Cl | 215-225 |
| 10.004 | Cl | O | 2-Cl | 195-198 |
| 10.005 | Cl | O | 4-OCH$_3$ | 210-215 |
| 10.006 | Cl | O | 3-OCH$_3$ | 182-188 |
| 10.007 | Cl | O | 2-OCH$_3$ | 155-160 |
| 10.008 | OCH$_3$ | O | 4-OCH$_3$ | 155-158 |

TABLE 11

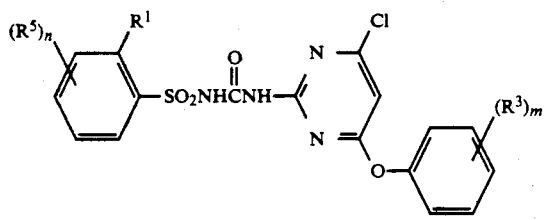

| No. | $R^1$ | $(R^5)_n$ | $(R^3)_m$ | Melting point (°C.) |
|---|---|---|---|---|
| 11.001 | CO$_2$(i-C$_3$H$_7$) | H | 3-OCH$_3$ | 130-133 |
| 11.002 | CO$_2$CH$_3$ | 5-F | 3-OCH$_3$ | 156-158 |
| 11.003 | CO$_2$CH$_3$ | 5-F | 2-OCH$_3$ | 125-127 |
| 11.004 | CO$_2$CH$_3$ | 3-Cl | 3-OCH$_3$ | 132 |
| 11.005 | CO$_2$CH$_3$ | 3-Cl | 4-OCH$_3$ | 192-194 |
| 11.006 | CO$_2$CH$_3$ | 5-F | 4-OCH$_3$ | 178-179 |
| 11.007 | CO$_2$(CH$_2$)$_2$Cl | H | 3-OCH$_3$ | 148 |
| 11.008 | CO$_2$(CH$_2$)$_2$Cl | H | 2-OCH$_3$ | 166-167 |
| 11.009 | CO$_2$(CH$_2$)$_2$Cl | H | 4-OCH$_3$ | 172-173 |
| 11.010 | CO$_2$(i-C$_3$H$_7$) | H | 2-OCH$_3$ | 143-145 |
| 11.011 | CO$_2$CH$_3$ | 3-Cl | 2-OCH$_3$ | 168-170 |
| 11.012 | CO$_2$(CH$_2$)$_2$CH$_3$ | H | 2,6-(OCH$_3$)$_2$ | 70-80 |

TABLE 12

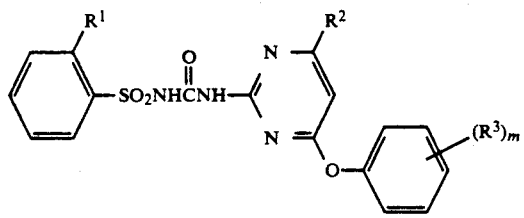

| No. | $R^2$ | X | $(R^3)_m$ | Melting point (°C.) |
|---|---|---|---|---|
| 12.001 | CO$_2$CH$_3$ | F | 2-OCH$_3$ | 161 |
| 12.002 | CO$_2$CH$_3$ | F | 3-OCH$_3$ | 143 |
| 12.003 | CO$_2$CH$_3$ | F | 4-OCH$_3$ | 167-170 |
| 12.004 | CO$_2$CH$_3$ | CF$_3$ | 2-OCH$_3$ | 115 |
| 12.005 | CO$_2$CH$_3$ | CF$_3$ | 3-OCH$_3$ | 177-178 |
| 12.006 | CO$_2$CH$_3$ | CF$_3$ | 4-OCH$_3$ | 188 |
| 12.007 | CO$_2$CH$_3$ | CF$_3$ | 3-N(CH$_3$)$_2$ | 176-177 |
| 12.008 | CO$_2$CH$_3$ | OC$_2$H$_5$ | 2-OCH$_3$ | 109 |
| 12.009 | CO$_2$CH$_3$ | OC$_2$H$_5$ | 3-OCH$_3$ | 71-75 |
| 12.010 | CO$_2$CH$_3$ | OC$_2$H$_5$ | 4-OCH$_3$ | 128-131 |
| 12.011 | CO$_2$CH$_3$ | OC$_2$H$_5$ | 3-N(CH$_3$)$_2$ | 142 |

USE EXAMPLES

The action of the sulfonylureas of the formula I on the growth of plants is demonstrated by the following greenhouse experiments.

The vessels employed were plastic flowerpots having a volume of 300 cm$^3$ and filled with a sandy loam containing about 3.0% humus. The seeds of the test plants were sown separately, according to species.

The plants were kept in the greenhouse in accordance with their specific requirements (10-25° C., and 20-35° C.) The experiments were run for from 2 to 4 weeks. During this period the plants were tended and their reactions to the various treatments assessed.

For the postemergence treatment, plants were selected which had been sown in the vessels and grown there, or they were grown separately as seedlings and transplanted to the vessels a few days before treatment. The plants were grown, depending on growth form, to a height of 3 to 15 cm before being treated with the compounds suspended or emulsified in water, and sprayed through finely distributing nozzles. The application rates for postemergence treatment were 0.5, 0.25 and 0.125 kg/ha.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients. The application rate in this treatment method was 0.125 kg/ha.

The assessment scale was 0 to 100, 100 denoting nonemergence or complete destruction of at least the visible plant parts, and 0 denoting no damage or normal growth.

The plants employed for the experiments were Amaranthus retroflexus, Chrysanthemum corinarium, Cyperus iria, Galium aparine, Helianthus annuus, Sesbania exaltata, Stellaria media and Triticum aestivum.

Compounds 1.002, 1.003 and 1.006, applied postemergence at rates of 0.5 and 0.25 kg/ha, combat unwanted plants very well.

Compounds 5.005 and 6.003, applied pre- and postemergence at a rate of 0.125 kg/ha, provide excellent control of unwanted broadleaved plants without causing any appreciable damage to the crop plant wheat.

We claim:

1. A substituted sulfonylurea of the formula I

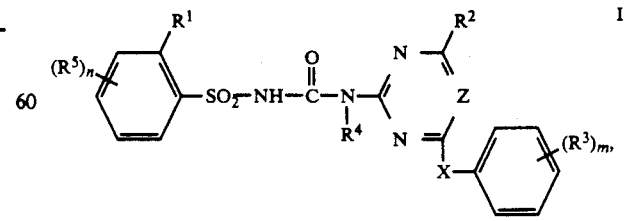

where the substituents and indices have the following meanings:

X is oxygen or sulfur;

Z is methine (=CH—);

$R^1$ is halogen, $C_1$-$C_4$-alkoxycarbonyl which may carry from one to three of the following radicals: halogen, $C_1$-$C_4$-alkoxy, $C_1$-$C_4$-haloalkoxy, $C_1$-$C_4$-alkylthio and/or $C_1$-$C_4$-haloalkylthio; $C_1$-$C_3$-alkoxy which may carry from one to three of the following radicals: halogen, $C_1$-$C_4$-alkoxy, $C_1$-$C_4$-haloalkoxy, $C_1$-$C_4$-alkylthio, and/or $C_1$-$C_4$-haloalkylthio; or a radical —$CONR^6R^7$, where $R^6$ is hydrogen, $C_1$-$C_8$-alkyl or $C_1$-$C_6$-alkoxy and
$R^7$ is hydrogen or $C_1$-$C_8$-alkyl;

$R^2$ is halogen; $C_1$-$C_4$-alkoxy or $C_1$-$C_4$-alkyl which may each carry from one to three of the following radicals: halogen, $C_1$-$C_4$-alkoxy and/or $C_1$-$C_4$-alkylthio;

$R^3$ is $C_1$-$C_4$-alkyl, $C_1$-$C_1$-alkoxy, $C_1$-$C_4$-alkylthio, $C_1$-$C_4$-haloalkyl, $C_1$-$C_4$-haloalkoxy, $C_1$-$C_4$-haloalkylthio, halogen, cyano, nitro, amino, mono-$C_1$-$C_4$-alkylamino, di-$C_1$-$C_4$-alkylamino, $C_2$-$C_6$-alkenyl, $C_1$-$C_4$-alkoxycarbonyl, $C_1$-$C_4$-alkanoyl or benzyl; or, bonded to adjacent ring positions, member of the group consisting of pyrrolidinyl, piperidinyl, morpholinyl and thiamorpholinyl —OCRR′O—, where R and R′ are each hydrogen or $C_1$-$C_4$-alkyl;

$R^4$ is hydrogen or $C_1$-$C_4$-alkyl;

$R^5$ is halogen, $C_1$-$C_4$-alkyl, $C_1$-$C_4$-alkoxy, $C_1$-$C_4$-alkylthio or $C_1$-$C_4$-haloalkyl;

m is from 0 to 3 or, when $R^3$ is halogen, from 0 to 5, differences among the $R^3$ radicals being possible when m is 2 or 3; and n is from 0 to 2, a difference between the $R^5$ radicals being possible when n is 2;

and environmentally acceptable salts thereof.

2. A herbicidal composition containing a herbicidally effective amount of substituted sulfonylurea as set forth in claim 1, or a salt thereof, and conventional formulation auxiliaries.

3. A process for combating the growth of unwanted plants, wherein a herbicidally effective amount of a substituted sulfonylurea as set forth in claim 1, or a salt thereof, is applied to the plants and/or their habitat.

4. A composition for influencing the growth of plants, containing a growth-regulating effective amount of a substituted sulfonylurea as set forth in claim 1, or a salt thereof, and conventional formulation auxiliaries therefor.

5. A process for influencing the growth of plants, wherein a growth-regulating amount of a substituted sulfonylurea as set forth in claim 1, or of a salt thereof, is applied to the plants and/or their habitat.

* * * * *

UNITED STATES PATENT AND TRADEMARK OFFICE
CERTIFICATE OF CORRECTION

PATENT NO. : 5,032,167
DATED : Jul. 16, 1991
INVENTOR(S) : Horst MAYER et al.

It is certified that error appears in the above-identified patent and that said Letters Patent is hereby corrected as shown below:

On the Cover Page:

In the Abstract:

That part reading "$R^3$ is $C_1-C_4$-alkyl, $C_1-C_4$-alkylthio" should read -- $R^3$ is $C_1-C_4$-alkyl, $C_1-C_4$-alkoxy, $C_1-C_4$-alkylthio --

Claim 1, Col. 35, Lines 21-23:

That part reading "benzyl; or, bonded to adjacent ring positions, member of the group consisting of pyrrolidinyl, piperidinyl, morpholinyl and thiamorpholinyl" should read -- benzyl; a member of the group consisting of pyrrolidinyl, piperidinyl, morpholinyl and thiamorpholinyl; or bonded to adjacent ring positions, --

Signed and Sealed this

Eighth Day of December, 1992

*Attest:*

DOUGLAS B. COMER

*Attesting Officer*   Acting Commissioner of Patents and Trademarks